US006574501B2

(12) United States Patent
Lambert et al.

(10) Patent No.: US 6,574,501 B2
(45) Date of Patent: Jun. 3, 2003

(54) ASSESSING BLOOD BRAIN BARRIER DYNAMICS OR IDENTIFYING OR MEASURING SELECTED SUBSTANCES OR TOXINS IN A SUBJECT BY ANALYZING RAMAN SPECTRUM SIGNALS OF SELECTED REGIONS IN THE EYE

(75) Inventors: James L. Lambert, Sunland, CA (US); Mark S. Borchert, La Canada, CA (US)

(73) Assignees: Childrens Hospital Los Angeles, Los Angeles, CA (US); California Institute of Technology, Los Angeles, CA (US)

( * ) Notice: Subject to any disclaimer, the term of this patent is extended or adjusted under 35 U.S.C. 154(b) by 0 days.

(21) Appl. No.: 09/756,897

(22) Filed: Jan. 9, 2001

(65) Prior Publication Data

US 2001/0034478 A1 Oct. 25, 2001

Related U.S. Application Data

(63) Continuation-in-part of application No. 09/690,113, filed on Oct. 16, 2000, which is a continuation of application No. 09/351,788, filed on Jul. 12, 1999, now Pat. No. 6,181,957.
(60) Provisional application No. 60/092,545, filed on Jul. 13, 1998.

(51) Int. Cl.[7] ................................................. A61B 6/00
(52) U.S. Cl. ........................................ 600/473; 600/475
(58) Field of Search ................................. 600/473, 475

(56) References Cited

U.S. PATENT DOCUMENTS

| 5,243,983 A | 9/1993 | Tarr et al. .................... 128/633 |
| 5,308,356 A | 5/1994 | Blackshear, Jr. et al. ... 606/194 |

(List continued on next page.)

FOREIGN PATENT DOCUMENTS

| WO | WO00/02479 | 1/2000 |

OTHER PUBLICATIONS

Borchert et al., *A Noninvasive Glucose Monitor: Preliminary Results in Rabbits,* Diabetes Tech. & Therapeu., 1(2):145–151 (1999).

(List continued on next page.)

*Primary Examiner*—Marvin M. Lateef
*Assistant Examiner*—Devaang Shah
(74) *Attorney, Agent, or Firm*—Myers Bigel Sibley & Sajovec PA

(57) ABSTRACT

A non-invasive method for analyzing the blood-brain barrier includes obtaining a Raman spectrum of a selected portion of the eye and monitoring the Raman spectrum to ascertain a change to the dynamics of the blood brain barrier.

Also, non-invasive methods for determining the brain or blood level of an analyte of interest, such as glucose, drugs, alcohol, poisons, and the like, comprises: generating an excitation laser beam (e.g., at a wavelength of 600 to 900 nanometers); focusing the excitation laser beam into the anterior chamber of an eye of the subject so that aqueous humor, vitreous humor, or one or more conjunctiva vessels in the eye is illuminated; detecting (preferably confocally detecting) a Raman spectrum from the illuminated portion of the eye; and then determining the blood level or brain level (intracranial or cerebral spinal fluid level) of an analyte of interest for the subject from the Raman spectrum. In certain embodiments, the detecting step may be followed by the step of subtracting a confounding fluorescence spectrum from the Raman spectrum to produce a difference spectrum; and determining the blood level and/or brain level of the analyte of interest for the subject from that difference spectrum, preferably using linear or nonlinear multivariate analysis such as partial least squares analysis. Apparatus for carrying out the foregoing methods are also disclosed.

57 Claims, 20 Drawing Sheets

U.S. PATENT DOCUMENTS

| | | | | |
|---|---|---|---|---|
| 5,377,681 A | * | 1/1995 | Drane | 128/653.4 |
| 5,433,197 A | | 7/1995 | Stark | 128/633 |
| 5,521,392 A | | 5/1996 | Kennedy et al. | 250/492.1 |
| 5,535,743 A | * | 7/1996 | Backhaus et al. | 128/633 |
| 5,553,617 A | * | 9/1996 | Barkenhagen | 128/633 |
| 5,666,956 A | | 9/1997 | Buchert | 128/664 |
| 5,710,630 A | | 1/1998 | Essenpreis et al. | 356/345 |
| 6,181,957 B1 | * | 1/2001 | Lambert et al. | 600/319 |
| 6,223,069 B1 | * | 4/2001 | Pfeiffer et al. | 600/431 |
| 6,312,686 B1 | * | 11/2001 | Staddon et al. | 424/94.1 |

OTHER PUBLICATIONS

Erckens et al., *Raman Spectroscopy for Non–Invasive Characterization of Ocular Tissue: Potential for Detection of Biological Molecules*, Abstract, J. of Raman Spectroscopy, 28(5):293–9 (May 1997).

Schulze HG et al., *Artificial Neural Network and Classical Least–Squares Methods for Neurotransmitter Mixture Analysis*, Abstract, J. Neurosci Methods, 56(2):155–167 (Feb. 1995).

Wang et al., *Analysis of Metabolites in Aqueous Solutions by Using Laser Raman Spectroscopy*, Applied Optics, 32(6):925–929 (Feb. 20, 1993).

Wicksted et al., *Raman Spectroscopy Studies of Metabolic Concentrations in Aqueous Solutions and Aqueous Humor Specimens*, Applied Spectroscopy, 49(7):987–993 (1995).

Sahagian, R., *Master Bond Adhesives, Sealants & Coatings*, Critical Insight: Marking Devices with Radiopaque Coatings (MDDI archive, May 1999), wysiwyg://13//http://www.devicelink.com/mddi/archive99/05/011.html (Mar. 21, 2001).

Schrader et al., *The Glucose Content of the Aqueous Humor Compared with Capillary Blood in Man*, Invest. Ophthalmol. Vis. Sci. (Suppl.), 44:404 (2000).

Auclair et al., Comparitive pharmocokinetics of D– and L–alphamethyldopa in plasma, aqueous humor, and cerebrospinal fluid in rabbits. Fundam. Clin. Pharmmacol. 2:283–293, 1988.

Berger et al., An enhanced algorithm for linear multivariate calibration. Anal. Chem. 1998; 70: 623–627.

Berger et al., Analytical method of calculating chemometric predition error. J. Appl. Spectrosc. 51:725–732, 1997.

Berger et al., Multicomponent blood analysis by near–infrared Raman spectroscopy. Applied Optics 38:2916–1926, 1999.

Bito, et al., Transport of prostaglandins across the blood–brain and blood–aqueous barriers and the physiological significance of these absorptive transport processes. Exp Eye Res. 25 Suppl (4):225–249, 1977.

Buono, M. J., Sweat ethanol concentrations are highly correlated with co–existing blood values in humans Exp. Physiol. 84:401–404, 1999.

Geladi et al., Partial least squares regression: A tutorial. Analytica Chimica Acta. 1986; 185:1–17.

Grabner et al., The blood–aqueous barrier and its permeability for proteins of different molecular weight. 207":137–148, 1978.

Haaland et al., Partial least squares methods for pectral analysis. 1. Relation to other quantitative calibration methods and the extraction of qualitative information. Anal. Chem. 1988: 60; 1193–1210.

Lambert et al., Measurement of physiologic glucose levels using Raman spectroscopy in a rabbit aqueous humor model. LEOS Newsletter 12:19–22, 1998.

Lobanov et al., Analysis of ethanol–glucose mixtures by two microbial sensors: application of chemometrics and artificial neural networks for data processing. Bisens. and Bioelectro. 16:1001–1007, 2001.

Marose et al., Optical Senson systems for bioprocess monitoring. Trends in Biotechnology 17:30–34, 1999.

Marquardt et al., A Raman waveguide detector for liquid chromatography. Anal Chemistry 71:4808–4814, 1999.

Mian et al., Comparison of fluconazole pharmacokinetics in serum, aqueous humor, vitreous humor, and cerebrospinal fluid following a single dose and at steady state. J. Ocul. Pharmacol. Ther. 14:459–471, 1998.

Pelletier et al., Efficient elimination of fluorescence background from Raman spectra collected in a liquid core optical fiber. Applied Spectroscopy 54: 1837–1841, 2000.

Rebrin et al., Subcutaneous glucose predicts plasma glucose independent of insulin: implications for continuous monitoring. Am J. Physiol. Endo. Metab. 277:E561–E571, 1999.

Schlingemann et al., Ciliary muscle capillaries have blood–tissue barrier characteristics. Exp. Eye Res. 66:747–754, 1998.

Shaw et al., Noninvasive, on–line monitoring of the biotranformation by yeast of glucose to ethanol using dispersive Raman spectroscopy and chemometrics. Applied Spectroscopy 53:1419–1428, 1999.

Sivakesava et al., Monitoring a bioprocess for ethanol production using FT–MIR and Ft–Raman spectroscopy. Journal of Industrial Microbiology and Biotechnology 26:185–190, 2001.

Unger et al., Disruption of the blood–aqueous barrier following paracentesis in the rabbit. Exp. Eye Res. 20:255–270, 1975.

Walfren et al., Appl. Spec. 1972, 26:585.

Wientjes et al, Determination of time delay between blood and interstitial adipose tissue glucose concentration change by microdialysis in healthy volunteers. Int. J. Artificial Organs 24:884–889, 2001.

* cited by examiner

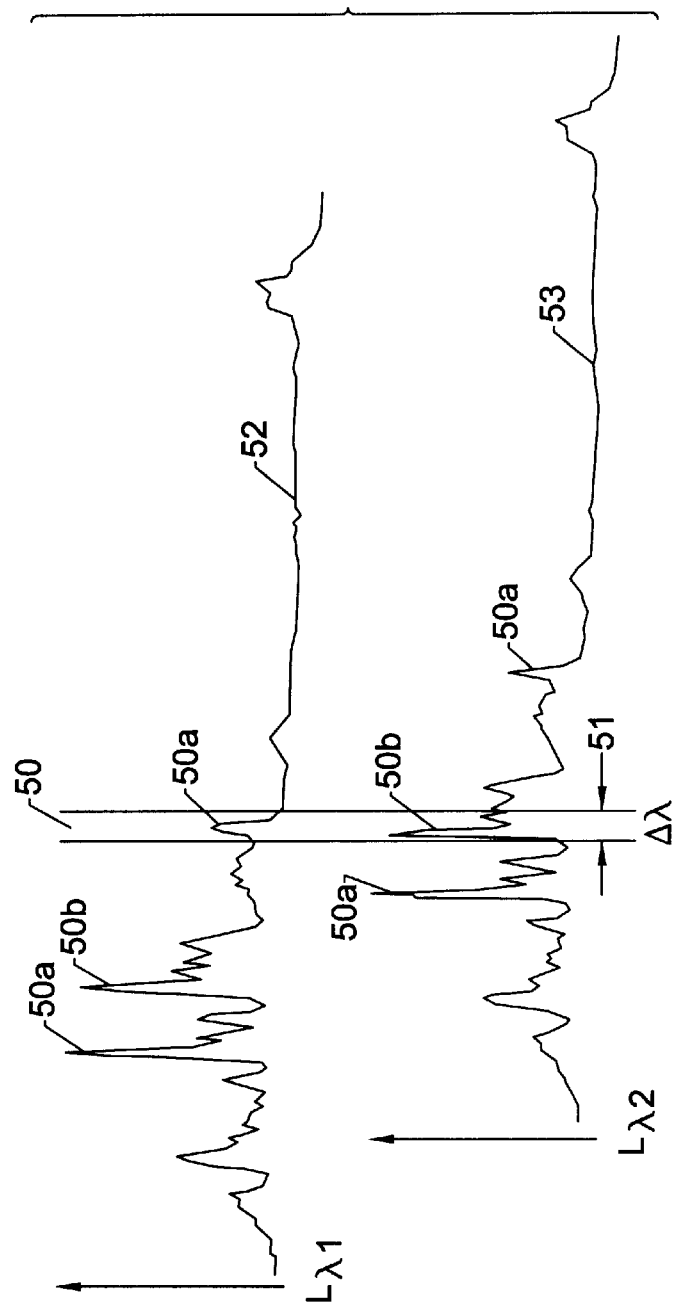

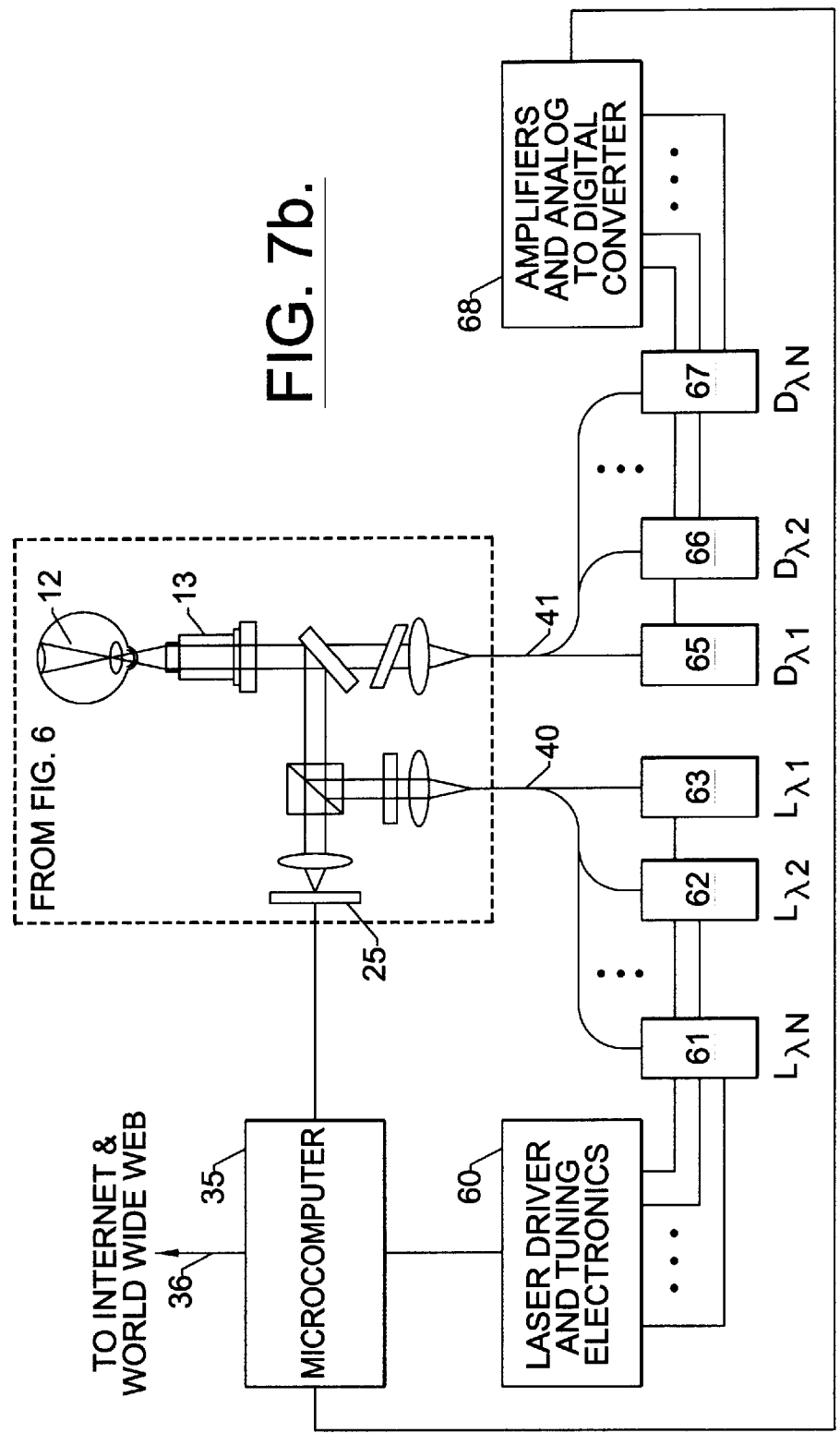

Optical power density calculations are performed using a canonical model of the adult eye (20A). a ray-tracing technique is used to calculate the area of retina exposed, $A$, by treating the incident light as if it emanated from node point $N$. Equation 1 is an expression of $A$ as a function of $\theta_c$ and the radius of the globe $R$ (20B). Equation 2 is derived in0order to express $\theta_c$ in terms of the angle of incidence $\theta_i$. Equation 2 must be solved numerically for $\theta_c$. Substituting $\theta_c$ into Equation 1 is used to determine $A$. Power density is easily calculated for a given input power once $A$ is determined. Solutions for both the exposed retinal area and the power density (assuming 30 mW input) are shown as a function of the angle of incidence (20C).

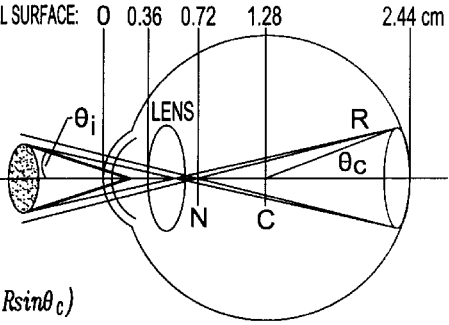

FIG. 20A.

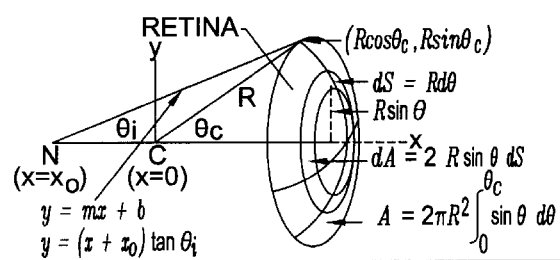

FIG. 20B.

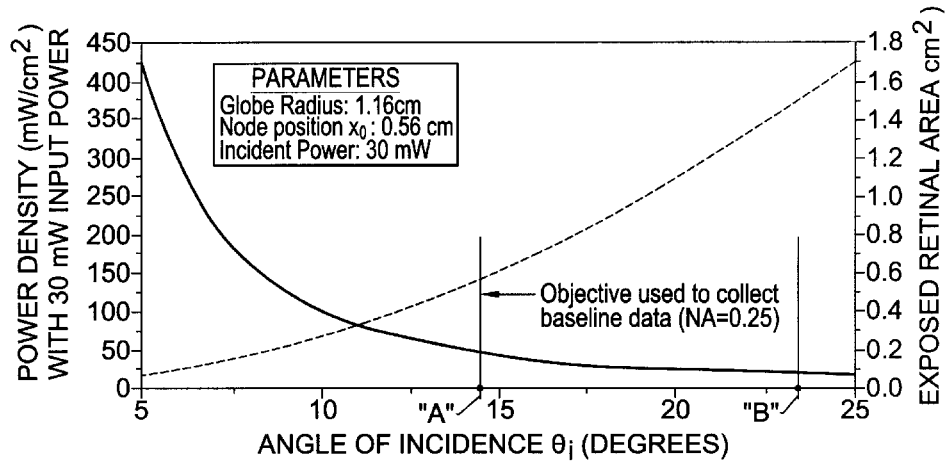

FIG. 20C.

ASSESSING BLOOD BRAIN BARRIER DYNAMICS OR IDENTIFYING OR MEASURING SELECTED SUBSTANCES OR TOXINS IN A SUBJECT BY ANALYZING RAMAN SPECTRUM SIGNALS OF SELECTED REGIONS IN THE EYE

RELATED APPLICATIONS

This application is a continuation-in-part of U.S. application Ser. No. 09/690,113, filed Oct. 16, 2000, which is a continuation of U.S. application Ser. No. 09/351,788, filed Jul. 12, 1999, now U.S. Pat. No. 6,181,957 which claims the benefit of U.S. Provisional Application No. 60/092,545, filed Jul. 13, 1998, the disclosures of which are hereby incorporated by reference as if restated in their entirety herein.

The invention described herein was made in the performance of work under a NASA contract, and is subject to the provisions of Public Law 96-517 (35 USC §202) in which the Contractor has elected to retain title. The United States Government has certain rights to this invention.

FIELD OF THE INVENTION

The present invention concerns methods and apparatus for measuring or identifying the presence of selected substances in the body and/or assessing blood brain dynamics of a subject via non-invasive spectrographic analysis of certain regions of the eye, such as the aqueous humor in the anterior chamber of the eye.

BACKGROUND OF THE INVENTION

Non-invasive measurement of physiological and foreign substances, including blood glucose, by optical spectroscopy techniques has remained an elusive target for at least two decades. Blood, tissue, and most excreted fluids contain numerous substances which confound many spectral signatures. On the other hand, the aqueous humor (AH), which fills the anterior chamber of the eye (between the lens and cornea), contains relatively few molecules capable of interfering with the spectroscopic detection of glucose. These are primarily lactate, ascorbate, and urea. This fact, along with its optically accessible location behind the cornea, makes the AH an attractive choice as a site on which to attempt non-invasive analysis of many substances present in a biological subject, including glucose.

Pohjola (*Acta Ophthalmologica Suppl.* 88, 1–80 (1996)) showed that the ratio of aqueous glucose to plasma glucose in normal euglycemic individuals is related to age and ranges from 0.6 to 0.9. He further showed in seven humans with steady-state hyperglycemia that similar ratios applied. There is little, if any, data regarding the equilibration time of aqueous humor glucose with changes in plasma glucose in humans. Some recent research suggests that the glucose content of the AH compared with that in the capillary blood in man is about 0.75 regardless of the glycemic state of the person. See e.g., Schrader et al., *The glucose content of the aqueous humour compared with capillary blood in man,* Invest. Ophthalmol. Vis. Sci. (Suppl.) 44:404 (2000).

Numerous investigators over the years have suggested that the ratio of aqueous glucose to plasma glucose in the normoglycemic rabbit ranges from 0.42 to 1.01 (S. Pohjola, supra; D. Reddy and V. Kinsey, *Arch. Ophthalmol.* 63, 715–720 (1960); M. Reim et al., *Ophthalmologica* 154, 39–50 (1967); W. March et al., *Diabetes Care* 5, 259 (1982)). It is uncertain whether this variability is normal or could be attributed to differences in glucose measurement techniques, collection techniques, sample storage, and anesthesia. It is believed that the relationship of aqueous glucose to rising, or falling, plasma glucose has not been previously studied in rabbits.

Coté has reviewed the relative strengths and weaknesses of optical glucose sensing techniques (*J. Clin. Engineering* 22, 253 (1997)). Raman spectroscopy is potentially attractive because it can distinguish glucose in water solutions containing various levels of other optically active metabolites (S. Wang et al., *Applied Optics* 32, 925 (1993)). Raman spectroscopy measures the shift in the wavelength of incident light as it is scattered by molecules. Any given molecule typically causes a characteristic shift in the spectrum of scattered light, which is dependent upon its intermolecular and intramolecular bonds. This is in contradistinction to fluorescence, which is caused by changes in electron energy states, and does not shift relative to the wavelength of incident light.

Wicksted et al, (*Appl. Sectroscop.* 49, 987 (1995)) suggest that the Raman signature for glucose can be identified in aqueous humor samples, and Goetz et al. (*IEEE Trans. Biomed. Eng.* 42, 728 (1995)) have demonstrated that higher than physiologic levels of glucose can be measured with Raman spectroscopy in water solutions. J. Lambert et al. (*LEOS Newsletter* 12, 19–22 (1998)) suggest that measurement of glucose at physiologic levels is possible in water solutions containing other analytes normally found in the aqueous humor. In certain situations, when solutions containing fluorescent substances are studied, however, the fluorescence signal may overwhelm the relatively weak Raman-shifted signal. This is a potential problem if Raman spectroscopy is applied to certain regions in the eye, such as the conjunctiva or vitreous or aqueous humor (and/or depending upon what the Raman signal is attempting to identify or measurer), which can contain proteins that fluoresce.

U.S. Pat. No. 5,243,983 to Tarr et al. proposes a non-invasive blood glucose measurement system using stimulated Raman spectroscopy. Stimulated Raman spectroscopy can require the use of both a pump and a probe laser beam. In operation, the probe laser beam is used to measure the stimulated Raman light at a single wavelength after transmission across the anterior chamber of the eye. Commercially, this may be undesirable, since an optical component contacting the eye is used to direct the beam across the anterior chamber. In addition, use of a single wavelength may limit the ability to measure glucose at physiologic levels within tissue containing many other Raman scattering chemicals.

Others have also proposed various glucose measurement devices. For example, U.S. Pat. No. 5,433,197 to Stark suggests a non-invasive glucose measurement apparatus that employs broadband, infrared light stimulation. In addition, U.S. Pat. No. 5,553,617 to Barkenhagen proposes a non-invasive method for measuring body chemistry from the eye of a subject by measuring a spectral response such as a Raman scattering response. While the latter reference alleges that it may be used for medical applications (such as the determination of sugar in diabetics), specific details on how this might be accurately carried out are not provided. Another example is found in U.S. Pat. No. 5,710,30 to Essenpreis, which proposes a method for measuring the concentration of glucose in a biological sample such as the eye (see FIG. 4 therein) with interferometric measurement procedures. Still another example is proposed in U.S. Pat. No. 5,666,956 to Buchert et al., wherein it is proposed that an instrument for the non-invasive measurement of a body analyte can be based on naturally emitted infrared radiation.

In spite of the foregoing efforts, a commercially viable, non-invasive monitor which can successfully employ a non-invasive optical analysis of certain regions of the eye, including the aqueous humor of the eye, has not yet been developed. Difficulties in developing such a device include: (a) determining reliable correlations of the typical millimolar quantities of selected substances or chemicals; (b) obtaining accurate measurements of selected substances; and (c) inhibiting damaging effects to the eye which may be caused by excessive exposure to light in an instrument that is used to generate the analysis signal spectrum in the AH. Accordingly, there is a continued need for improved systems, methods, and devices for the non-invasive in vivo analysis of foreign and natural physiologic substances in a biological subject via optical analysis of certain regions of the eye.

SUMMARY OF THE INVENTION

The present invention provides methods and systems for monitoring or evaluating the blood aqueous barrier and, thus, the blood brain barrier dynamics of the subject. The present invention also provides methods which can detect the presence or absence of one or more selected substances or analytes of interest in the body by optically analyzing certain regions of the eye, including at least one of the AH, the vitreous humor ("VH"), and one or more blood vessels in the conjunctiva. In certain embodiments, the analysis can provide information regarding the presence of and/or quantify a detected substance in the cerebral spinal or intracranial fluid of the subject (indirectly, through a correlation with the presence or quantification of the substance in the blood vessel in the conjunctiva, or the AH or the vitreous humor).

Embodiments of the invention can employ Raman spectroscopy to non-invasively obtain, in vivo, at least one signature spectroscopic signal to identify and/or measure the level or concentration of a substance or substances of interest in the subject (either in the blood and/or brain) based on the signal.

In certain embodiments, the present invention can be used to monitor or evaluate the blood brain barrier dynamics, which may be intentionally altered (such as through the administration of chemicals or exposure to certain environmental conditions such as increased pressure) during such evaluation. By intentionally breaking down the blood brain barrier, medicines which are normally inhibited from crossing the barrier may be allowed to more readily cross and enter into the brain. To monitor such a change in the operation or dynamics of the blood brain barrier, non-specific markers can be introduced or injected into the subject. The non-specific marker is selected based on its molecular size and/or its normal reluctance to cross the blood brain barrier. The blood brain barrier can then be intentionally altered (broken down or opened) so that the non-specific marker is able to cross therethrough. An optical reading of a selected region of the eye can be taken, and the present invention can assess whether the marker is present (either at all or in an increased amount over a pre-alteration state) in the blood aqueous barrier. Further, in some embodiments, the concentration of the marker in the eye can be determined (such as in the AH or vitreous humor) in the blood aqueous compartment. If the marker is identified as being present, this indicates that the blood brain barrier has been altered. Once the blood brain barrier is altered, a desired treatment regimen can be administered to the subject (such as drug used for chemotherapy) to treat tumors or other conditions in the eyes or brain. In some embodiments, as an alternative to the use of non-specific markers, the present invention can monitor the presence or concentration of the treatment drug itself in the blood aqueous compartment in the eye. Examples of suitable markers include large molecule natural and synthetic substances which do not normally cross the blood brain barrier, including, but not limited to, antibiotics such as erythromycin, and conjugated substances such as conjugated billirubin.

Typically, the treatment drug is configured such that it is inhibited from crossing the blood brain barrier. Thus, in certain applications, in order to deliver a sufficient quantity of the drug to the brain, the amount of drug, which is systemically delivered, can be undesirably toxic to the patient away from the targeted treatment region in the brain. The present invention can now assess or assure either that the barrier is sufficiently altered to allow the drug to pass more efficiently therethrough and/or quantify or assess that a sufficient amount of the treatment drug is getting into the brain so that the systemic amount can be more closely regulated and reduced. After the desired treatment (or dose) is indicated as delivered to the brain, the blood brain barrier can be restored such that it is substantially in its pre-altered state. The return to the pre-altered state can be confirmed by taking another optical reading to confirm that the marker is in a reduced concentration in the blood aqueous compartment in the eye.

By identifying and/or quantifying the amount of the non-specific marker present in the aqueous humor (and, thus, in the blood aqueous barrier), an estimate or determination of the concentration in the brain can be established. Typically, the concentration in the blood aqueous humor can be presumed to be similar to that in the blood brain compartment. Further, the two concentrations can be correlated so that a quantitative value of the amount in the cerebral spinal or intracranial fluid can be determined based on that found in the blood aqueous compartment so that a titrated dose of the treatment drug in the brain may be able to be determined. The correlation relationship or ratio may vary within certain population segments. In certain embodiments, the correlation relationship can be determined based on data collected across a representative population (by age, size, weight, gender, race, disease or physiological impairment or abnormality, or national origin). Thus, the amount of the selected treatment drug actually getting into the brain can be correlated to the systemic dose delivered to the patient so that the dose or level in the spinal fluid is sufficiently high for treatment of the tumor or other condition but the systemic dose is sized to provide reduced toxicity to the subject (by avoiding administering unnecessary quantities to the subject).

In certain embodiments, the present invention can provide methods, similar to that discussed for intentionally altering the dynamics of the blood brain barrier, which use a non-specific marker with a new drug to evaluate the impact that a new drug or therapy regimen has on the blood brain barrier for safety or other considerations. In other embodiments, the optical detection of the drug itself in certain regions of the eye, without the use of a marker, may be sufficient to indicate the drug's impact on the blood brain barrier.

In other embodiments, the environmental conditions surrounding the patient or subject, can be altered and the dynamics of the blood brain barrier monitored. For example, subjects which are exposed to different elevations, gravity conditions, or to increased intracranial pressure, may exhibit different or altered blood brain barrier characteristics, either transiently, or more chronically, than persons not so exposed. These subjects may include astronauts, pilots, divers, trauma victims, and the like. Evaluating the blood brain barrier dynamics can identify whether larger molecules or pathogens are able to cross the blood brain barrier, which may, under normal circumstances, be inhibited or prevented from entering the brain. In certain embodiments, the present invention can be used to assess which constituents in the blood cross into the intracranial fluid via the blood brain barrier.

As generally described above, in one embodiment, a patient can undergo a treatment regimen to deliberately or intentionally alter the blood brain barrier dynamics so that an identified treatment agent(s) is allowed to cross the barrier. For example, an osmotic agent such as a drug (for example, MANATOL) can be delivered to a subject being treated for cancer to force the blood brain barrier to open (preferably for a limited-time treatment window) to successfully allow a selected chemotherapeutic agent (such as a cytotoxic agent) to be able to more readily cross the blood brain barrier into the brain. Non-invasive monitoring of the tumor dose according to the present invention, can allow monitoring of the barrier dynamics and may, in some embodiments, be able to assess when an adequate, but not excessive, tumor dose is delivered to the brain. The blood brain barrier can be reestablished after the appropriate tumor dosing is delivered. This monitoring of the blood brain barrier dynamics during a treatment regimen may now inhibit or reduce systemic damage in the subject associated with the cytotoxic treatment.

In other embodiments, the present invention provides systems and methods for detecting the presence of a predetermined substance or identifying the presence of an unknown substance in the body of a subject. The substances which can be measured or identified are numerous and can be (a) natural physiologic analytes or chemicals, such as glucose, amino acids, peptides, antibodies, blood (typically using light outside the red spectrum), and/or (b) foreign substances such as medicaments, drugs, or poisons (whether legal or illegal, and whether prescription or over the counter). For example, the present invention can be used to assess the presence of targeted illegal substances, such as alcohol or illegal narcotics such as cocaine, pcp, marijuana, or to identify what toxin or poison a subject has injested out of a number of household or environmental toxins and/or poisons such as herbicides, pesticides, household cleaning products, petroleum products or other common house hold chemicals including benzene, ethylene glycol. The methods and systems of the instant invention may even be used to identify the presence of poisonous plants, insect toxins, and reptile or snake venom. The present invention may be configured to identify whether an unknown substance in a subject is one or more of toxins/agents associated with the most prevalent poison-related emergency room visits. For example, ethylene glycol, methanol, and acetaminophen.

In certain embodiments, the present invention can be used to quantify the amount of the substance in the subject, typically this embodiment may be particularly suitable for those substances ingested in relatively large quantities or those present in sufficient quantity in the selected region of the eye so as to be detectable in vivo, or so that the substance or analyte is present in physiological levels (in the blood or blood aqueous compartment) of above about 0.001% or above about 1–10 $\mu$molars, depending on the Raman active characteristics of the analyte of interest.

In addition, in certain embodiments, the devices and methods of the present invention may be used to detect increased or decreased levels of physiologic analytes such as caused by system impairments or reactions associated with dehydration, allergic reactions, or physiologic analytes associated with bacterial infections such as spinal meningitis, or to identify whether proteins or antibodies are present in elevated levels to identify a systemic response or a localized infection or disease in the eye or an immune system response, in the subject.

In certain embodiments, the systems and methods of the present invention may be able to detect or identify toxins released or emitted from foods contaminated with food poisoning bacteria such as $E$ $coli,$ salmonella (either in vivo or in vitro). Further, in some embodiments, the methods and systems of the present invent may be used to identify the presence of mad cow disease by analyzing certain regions of the eye (either in vitro or in vivo) such as by obtaining a Raman spectrum of a desired region of the eye analyzing the spectrum to detect the presence of small peptides or other markers associated with the disease. Other diseases may be able to be identified in vivo by the presence of a systemic reaction (such as an increased constituent level of a natural physiologic substance) in the subject. It is anticipated that such a method may be potentially used to assess whether the subject has contracted Lyme disease associated with deer tick bites or Rocky Mountain spotted fever.

In some embodiments, the invention can identify the presence of one or a plurality of household or environmental poisons in the subject in a relatively fast "triage" assessment to allow clinicians to determine the appropriate treatment in a timely manner. This can be particularly important for pediatric applications where the substance ingested may be difficult to ascertain for young children, and a relatively quick identification of a particular toxin or toxins ingested may allow more reliable or faster treatment decisions to be established.

One embodiment of the invention is directed to an in vivo method for monitoring the blood brain barrier dynamics of a subject, comprising the step of monitoring the dynamics of the blood brain barrier by non-invasively obtaining the Raman spectrum of a selected region in the eye of the subject. The method may also include the step administering a non-specific marker to the subject selected for its normal reluctance to cross the blood brain barrier under the normal condition. The monitoring step can comprise detecting the presence of the non-specific marker in the selected region of the eye of the subject.

In certain embodiments, the method can include the steps of: altering the dynamics of the blood brain barrier of the subject from a normal condition; and administering a quantity of a selected therapeutic agent to a subject for treatment of condition in the brain or neurological system after the altering step. It can also include the step of substantially returning the blood brain barrier to its normal state after a sufficient quantity of the therapeutic agent has been delivered to the brain. Similarly, the monitoring step can be performed before the therapeutic drug is administered to the subject and subsequently to confirm that the blood brain barrier is substantially returned to its normal condition. The method may also include the step of assessing the dose amount of the therapeutic agent delivered to the brain.

Certain embodiments of the present invention are directed to an in vivo a non-invasive method for determining the level of an analyte of interest in a biological subject. Raman spectroscopy can be used to obtain the signature of the substance in the eye (such as in the AH, VH, or blood vessel in the conjunctiva) and, in some embodiments, to measure the concentration of a natural physiologic or foreign substance, such as glucose and/or proteins, or drugs, alcohol, environmental or household toxins, in the subject. The method can include the steps of: (a) generating an excitation laser beam (e.g., at a wavelength of from about 600 to 900 nanometers); (b) focusing the excitation laser beam into the eye of the subject so that a selected region of the eye is illuminated; (c) detecting (preferably confocally detecting) a Raman spectrum from the illuminated region of the eye; (d) comparing the Raman spectrum from the detecting step to predetermined spectrums corresponding to different analytes of different concentrations; and (e) identifying the presence of an analyte of interest based on the detecting and comparing steps.

In some embodiments, an additional step (f) can be performed to determine the blood or brain level of an analyte of interest for the subject from the Raman spectrum. The blood or brain level may be indirectly computated based on the concentration or amount of the analyte in the blood aqueous compartment (or can be directly measured in the blood itself for the conjunctiva vessel measurement). For the indirect measurement, that value can be correlated (or adjusted/corrected) to provide an assessment of the amount of the substance in the cerebral spinal fluid or blood. The correlation may be such that the amount of the substance directly measured in the AH is substantially similar to that in the cerebral spinal fluid. Alternatively, data correlating the relationship can be established and an empirical or statistical model established.

Although not required, in some embodiments, the detecting step can be followed by the step of subtracting a confounding fluorescence spectrum from the Raman spectrum to produce a difference spectrum; and determining the blood level of the analyte of interest for the subject from that difference spectrum, preferably using linear or nonlinear multivariate analysis such as partial least squares or artificial neural network algorithms. This technique may be particularly suitable where fluorescence is problematic for optical measurements taken directly of the blood level (i.e., by focusing at the blood vessels in the conjunctiva or at the vitreous humor).

In certain embodiments, a low energy excitation wave can be used to generate the Raman signal spectrum. "Low energy", as used herein, means power which is on the order of about 10–400 mJ or less, and typically between about 70–330 mJ. The energy exposure will depend on the power and pulse length of the excitation pulse. Longer wavelength pulses (i.e., above 700) may be used, typically with energy levels closer to the higher end of the scale, while lower wavelengths (600–700) may be used with lower energy exposure levels. In one embodiment, a wavelength of about 633 nm can be used for a pulse of about 5–10 seconds corresponding to about a 2–5 mW power exposure level (and between a 10–20 or 25–50 mJ energy exposure to the patient's eye (or eyes)) for each measurement or monitoring signal obtained. In other embodiments, an optical excitation pulse may have a 785 nm wavelength, a pulse length of about 20 ms–5 s and a power rating of about 14–16 mW. In one embodiment, a 5 sec, 16 mW pulse can be used to obtain the in vivo reading of a cancer agent in the selected region of the eye (typically the AH).

In some embodiments, the excitation beam can be transmitted such that it presents a reduced energy/density exposure rating to the tissue of the eye by shaping the beam to increase the cone angle or span of the excitation beam as it enters the eye to expose more of the area of the retina and reduce the energy/area rating of the excitation pulse to provide improved margins of safety (placing the energy/area rating sufficiently below the threshold of damage). In other embodiments, the transmission path numerical aperture is substantially matched to the return path numerical aperture (of the spectrometer).

A second aspect of the present invention is an apparatus for the non-invasive in vivo determination of the blood level of an analyte of interest in a subject. The apparatus includes a laser source for generating an excitation laser beam (e.g., at a wavelength of from about 600 to 900 nanometers) and an optical system (e.g., a confocal optical system) operatively associated with the laser for focusing the excitation laser beam into a selected region of the eye, including one or more blood vessels in the conjunctiva of the eye, the vitreous humor, or the anterior chamber of an eye (or eyes) of the subject so that the aqueous humor in the desired region of the eye is sufficiently illuminated. The apparatus also includes a detector operatively associated with the optical system and configured to detect a Raman spectrum from the selected illuminated region of the eye and a processor with computer program code for identifying the presence of one or more selected substances or analytes of interest. The computer code may also include code for determining the in vivo level of the analyte of interest in the selected region of the eye and to establish an estimate or measure of the analyte in the blood or cerebral spinal fluid to be established based on a correlation thereto for the subject from the Raman spectrum.

Focusing the optical analysis on the blood vessels in the conjunctiva can allow for a direct measurement of the substance in the blood, while the measurements taken from other portions of the eye can be correlated to provide an estimate or quantification of the substance in the blood and/or in the cerebral spinal fluid (i.e., indirect measurements). The correlation's can be established based on empirical models or actual measurements taken in vitro or in vivo on a representative animal or human population as is well known to those of skill in the art.

In certain embodiments, the apparatus can be configured as a low energy unit to inhibit the exposure of the tissue during the operation of the apparatus. The excitation wavelength at the low power may be less than 700 nm, such as about 633 nm.

Numerous additional features may be incorporated into the apparatus. The device may include a visual display screen for presenting visual indicia to the user, which can be individually adjusted and focused to the particular visual acuity of the subject (similar to vision screening focusing procedures). The apparatus may include a visual display screen for visually displaying the results of the test to the subject (such as through the same aperture or adjacent active matrix screen) as which the test is conducted. It may include a visual fixation target or device, also visible through the test aperture, which controls movement of the eye and simultaneously insures that focusing of the laser beam is properly directed into the anterior chamber of the eye. The processor may contain empirical models of actual testing experience to either determine the blood level or concentration of the analyte of interest or to identify the presence of selected substances. The apparatus may employ a laser of fixed wavelength, a tunable laser (which can sample a plurality of Raman scattered light (at different wavelengths) concurrently), a plurality of fixed wavelength lasers, or other light source means some of which can include means for sliding the Raman spectrum passed a plurality of different wavelength detectors to obviate the need for a full grating based Raman spectrometer (by taking a plurality of samples). The apparatus may include a wireless or remote communication line operably associated with the processor for transmitting the blood level of the analyte of interest to a remote location (such as for emergency home calls to an ER room).

Another aspect of the present invention is an in vivo method for administering drug or chemical therapy to a subject (such as for treatment of a cancerous tumor in the brain). The method includes the steps of: (a) administering a dose of a selected therapeutic agent to a subject; (b) altering the dynamics of the blood brain barrier from its normal state; (c) monitoring the dynamics of the blood brain barrier by non-invasively obtaining the Raman spectrum of a selected region in the eye (such as the vitreous or aqueous humor) and determining the quantity of the agent therein. The method may also include one or more of (d) estimating the dose of the therapeutic agent delivered to the brain (indirectly, based on the amount detected in the selected region of the eye) (e) repeating said monitoring step a plurality of times during the administering step; and (f) returning the blood brain barrier to its normal state after a sufficient quantity of agent has been delivered to the brain.

In one embodiment, the altering step can be carried out by introducing a chemical to the subject to temporarily open the blood brain barrier to allow larger molecules to pass therethrough. Further, the method can include the step of administering a non-specific marker which is reluctant to or does not normally pass through the blood brain barrier (i.e., is typically inhibited from passing therethrough). The optical analysis can monitor any increase (or the presence) of the non-specific marker in the selected region of the eye to confirm that the blood brain barrier dynamics has been altered.

In another embodiment, the altering step may be carried out by increasing the intracranial pressure of the subject.

Another aspect of the present invention is a method of non-invasively monitoring the blood brain barrier. The method comprises the steps of: (a) generating an excitation beam at a wavelength of from 600 to 900 nanometers; (b) focusing the excitation beam of said generating step into the anterior chamber of an eye of the subject so that aqueous humor in the anterior chamber is illuminated; (c) detecting a Raman spectrum corresponding to the illuminated aqueous humor; and (d) monitoring the AH to predict the behavior of the blood brain barrier dynamics during exposure to selected conditions based on the detecting step (based on the AH Raman spectrum analysis' indication of the presence or concentration of selected substances therein). It is anticipated that the correlation between the blood-aqueous and blood brain barrier is such that the presence and/or concentration in one can be extrapolated to that in the other.

Other embodiments focus the excitation beam such that it has an increased or wider cone angle to spread the light across more area of the retina. Still other embodiments are configured to focus to one or more blood vessels on the conjunctiva or to focus deeper to the vitreous humor.

In certain embodiments, the monitoring step can be used to assess whether the dynamics thereof alter sufficiently to allow selected analytes, which would normally be inhibited from traveling through the blood brain barrier, to pass into the intracranial spinal fluid through the blood brain barrier. In other embodiments, the monitoring step can be carried out when a person is under or exposed to extreme conditions such as when diving, flying, or mountain climbing, or when suffering from a traumatic head or brain injury, or high stress, and the like.

The method can also include the steps of comparing the Raman spectrum from the detecting step to reference spectrums corresponding to at least one selected analyte of interest; and identifying the presence of the least one analyte of interest in the subject based on the detecting and comparing steps in the selected region of the eye. The method may also be able to estimate the dose or affirm the presence of the analyte in the subject's cerebral spinal fluid.

Yet another aspect of the present invention is a method for identifying an alteration in the blood brain barrier of a biological subject, comprising the steps of: (a) non-invasively obtaining a first in vivo Raman spectrum of the aqueous humor of the subject; (b) non-invasively obtaining a second in vivo Raman spectrum of the aqueous humor of the subject; and (c) identifying an alteration in the blood brain barrier by comparing the first and second Raman spectrums.

An additional aspect of the present invention is a method for identifying an alteration in the blood brain barrier of a biological subject, comprising the steps of: (a) non-invasively obtaining a first in vivo Raman spectrum of the aqueous humor of the subject; (b) obtaining a reference spectrum of an in vitro sample representing the aqueous humor and comprising at least one selected analyte; and (c) comparing the in vivo Raman spectrum to the reference spectrum to identify an abnormality in the blood brain barrier by detecting the presence of at least one selected analyte in the AH thereby indicating its presence in the intracranial fluid of the subject.

The at least one selected analyte can be one which typically does not cross the blood brain barrier so that its presence is indicative of an abnormality or impairment or successful intentional alteration of the blood brain barrier dynamics.

Each of the embodiments of the invention may include computer program products and computational and look-up table associated therewith to identify the presence of the selected substance or substances of interest (and/or calculate the amount or concentration thereof) and to operate or control (regulate) the power of the excitation pulse emitted from the laser, and the illumination and detection of the scattered light. For example, in certain embodiments, the present invention can include a computer program product for determining the identity of an unknown substance in a subject. The product can comprise computer-readable program code comprising: (a) computer readable program code for defining at least one signature reference spectrum for at least one selected substance of interest; (b) computer readable program code for analyzing an in vivo obtained Raman spectrum of the aqueous humor of the subject; and (c) computer readable program code for based evaluating whether the in vivo Raman spectrum corresponds to at least one of the at lest one signature reference spectrums by comparing selected characteristics between the reference spectrum and the in vivo spectrum.

In various embodiments, the computer readable program code for defining the different reference spectrums can be for a particular one or a plurality of different selected substances. Examples of the selected substance(s) include, but are not limited to: alcohol, a substance banned for athletes in competition, a plurality of illegal narcotic substances, and a plurality of household products or common poisons for humans or animals which are potentially poisonous to a subject when ingested. A master look-up reference data base providing Raman spectrum data for a large quantity of different poisons or substances can be generated and stored at a central database or at local or regional offices, clinics or the like. The computer program can include means for remotely accessing the data such as via the use of an intranet or internet.

The present invention will now be described further and includes other features and analytes that can be included in the methods and apparatus described herein.

BRIEF DESCRIPTION OF THE DRAWINGS

FIG. 7a schematically illustrates the method of sliding Raman spectra features through a particular detector window by changing excitation frequency.

FIG. 7b schematically illustrates an apparatus of the invention that utilizes the method illustrated in FIG. 7a.

FIGS. 20A–20C illustrate optical power density calculations performed using a canonical model of the adult eye of a human. FIG. 20A is a model of the human eye. FIG. 20B is a schematic of a portion of the eye illustrating the angles an equations associated with power density. FIG. 20C is a graph of the power for exposed retinal area and the power density (assuming a 30 mW input) are shown as a function of the angle of incidence.

FIG. 21A corresponds to an ensemble spectrum of artificial aqueous humor samples in a model (artificial or test) anterior chamber. FIG. 21B corresponds to an in vitro ensemble spectrum of actual aqueous humor in a model anterior chamber. FIG. 21C corresponds to in vivo ensemble spectrum of aqueous humor.

DETAILED DESCRIPTION OF EMBODIMENTS OF THE INVENTION

Figure 1:
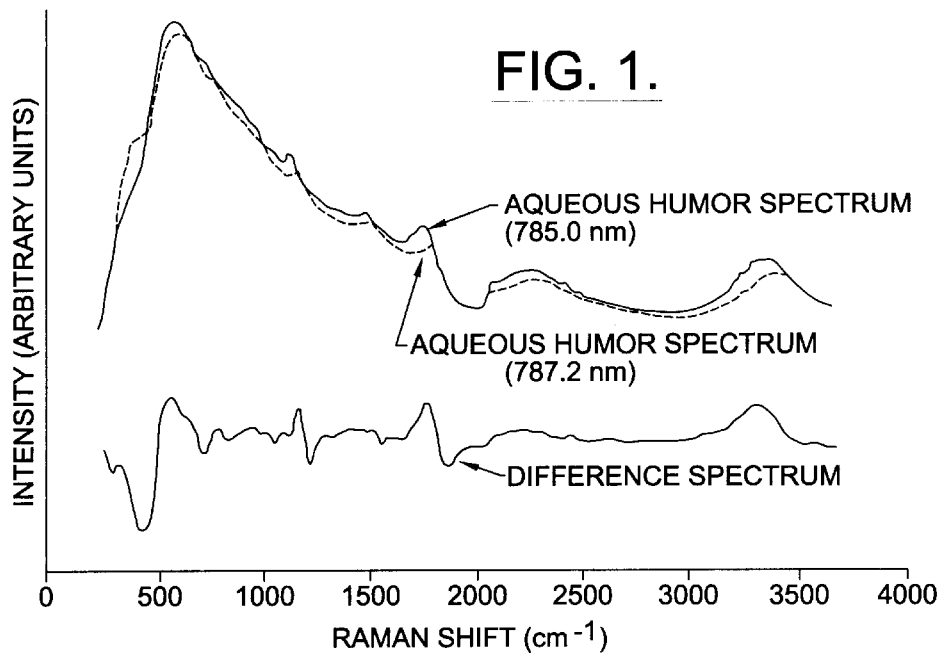
FIG. 1 is a graph which illustrates the broad spectrum of water in the aqueous humor, which, in some situations, can obscure the underlying peaks of interest in the Raman spectrum. The raw spectrum of rabbit aqueous humor is shown taken at 2 slightly different wavelengths (top). The difference spectrum (bottom) achieved by subtracting 1 raw spectrum from the other reveals a resultant bipolar Raman signature. Linear and/or nonlinear multivariate analysis can then be applied.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, layers, components, or features may be exaggerated for clarity.

The term "glucose" as used herein preferably refers to D-glucose. The term "subject"as used herein refers to both human subjects and animal subjects having circulatory systems including domestic large and small animals such as dogs, cats, rabbits, horses, cows, pigs, and the like. Animal subjects may be used in the present invention for veterinary purposes. The present invention may be particularly suitable for human subjects. The optical analysis may be performed on selected regions of the eye, including the blood vessels in the conjunctiva (i.e., one or more of the conjunctiva blood vessels located on the surface of the eye), the vitreous humor (the ("VH") or the aqueous humor (the "AH").

In certain embodiments, the present invention is primarily concerned with the determination of (a) the blood levels or (b) the brain fluid level, meaning the intracranial or cerebral spinal fluid levels, of selected substances or analytes of interest such as may be predicted by the presence and/or concentration of the substance or analyte in the selected region of the eye of a subject (typically, the AH or the conjuctiva vessel(s)).

In certain embodiments, the present invention recognizes that the mechanics of the blood aqueous barrier and the blood brain barrier are substantially the same such that, if the substance of analyte passes through the blood aqueous barrier, it can be presumed to also pass through the blood brain barrier. The correlation of the amount that passes through the blood brain barrier may be substantially equivalent to that detected in the eye or may be at a lesser or greater concentration. However, the blood concentration of other Raman-active molecules, analytes, or substances which do not typically pass through the blood brain barrier may also be determined by these techniques. Similarly, the amount or presence of the selected substance or molecule, etc., in the eye itself can be determined by these techniques (such as to treat localized in the eye or non-systemic diseases such as cancers of the eye).

As used herein, the term "analyte" is used interchangeably with "substance" to identify a selected target chemical, molecule or molecules, either in its blood-absorbed or partially absorbed, uptaken, or constituent form, or in an ex vivo formulation, where applicable. As such, the substance or analyte can include a chemical compound or composition, whether synthetic or natural, as well as a constituent thereof or molecule of interest. In some embodiments, the analyte or substance can be one that is emitted by the body (sometimes in an elevated amount) in response to a disease or physiologic reaction to a product or toxin and may also be a byproduct of the body's reaction to a substance. As such, as noted in the summary of the invention above, the substances which can be measured or identified according to the present invention are numerous and can include (a) natural physiologic substances, analytes or chemicals, such as glucose, amino acids, peptides, blood, or other components of or in blood, or in the eye and/or (b) foreign or synthetic or artificial substances such as medicaments, drugs, or poisons (whether legal or illegal, and whether prescription or over the counter) which may be present in the subject. For example, the present invention can be used to identify or assess the presence (or absence) of and/or the blood level or concentration of lactate, urea, benzene, ascorbate alcohol, ethanol, methanol, ethylene glycol, steroids, nicotine, or illegal narcotics such as cocaine, other opiate-based drugs, or prevalent or pervasive designer drugs, or metabolites, or household, organic, or environmental toxins and/or poisons such as herbicides, pesticides, household cleaning products, petroleum products or other chemicals.

For quantification purposes, the present invention may be particularly suitable for identifying the amount of substances, which present in the selected region of the eye in sufficient quantities to allow Raman based detection. For example, a substance which is present in an amount of at least about 1–10, and preferably about 10–100 $\mu$molars in the AH may be detectable, particularly if the substance is a Raman active molecule with enhanced resonance at a particular selected excitation light wavelength. In some embodiments, the targeted analyte may be present in the selected or targeted region of the eye in an amount of at least about 1 millimolar or in a physiological concentration level of about at least 0.001%. The present invention may also be able to identify the presence of, or a physiologic reaction to, substances associated with poisonous plants, insect or arachnid poison, and reptile or snake venom, in the subject.

In addition, in certain embodiments, the devices and methods of the present invention may be used (to analyze either iii vitro or in vivo) to detect increased or decreased levels of physiologic analytes in the blood or to detect certain disease processes of known conditions. For example, by identifying increased or decreased levels of certain substances in the body or the presence in the subject of certain peptides or toxins associated with a particular condition, such as those caused by system impairments or reactions associated with dehydration, allergic reactions, toxins from bacterial infections such as spinal meningitis, or elevated or decreased levels of antibodies to identify an immune system response, or even hormones evoked in response to a pregnancy.

In certain embodiments, the methods and devices of the present invention can be configured to (a) identify the presence of and/or (b) quantitatively estimate or determine the blood and/or cerebral spinal or intracranial concentration level of one or more selected substances in the subject. The quantitative assessment can include determining how much of the selected substance is crossing the blood brain barrier (based on a correlation to the amount present in the selected region of the eye, typically the AH). In other embodiments, the methods and devices of the invention can be used to dynamically monitor changes in the operation of the blood brain barrier (which may be altered intentionally for some embodiments of the invention).

In any event, generally stated, in operation, a laser excitation light signal is focused to and transmitted into a selected region in the eye. Typically, this will be the AH, but, in some embodiments, can also include either the blood vessel(s) in the conjunctiva or the vitreous humor. Illumination of the blood vessel(s) in the conjunctiva of the eye will not require as great a penetration depth as either the AH or the vitreous humor, while the vitreous humor will require the excitation light pulse to have an increased penetration depth over that of the AH and the conjunctiva to reach the vitreous humor in the eye.

In any event, after the selected region of the eye is illuminated, a corresponding Raman spectroscopic signal is obtained. Each selected substance can generate a "signature" spectrographic signal with different signature peaks at different frequencies. Higher concentrations will yield stronger signals. The subject's spectroscopic signal can then be digitally compared to a plurality of reference signals stored in computer memory. The reference signals correspond to one or more selected substances which can be predetermined from an in vitro analysis of the substance as it exists in a corresponding sample. For example, for the AH measurement, a representative eye AH can be a representative target phantom such as in artificial AH's, or test vials with known concentrations of the substance in a known solvent, such as a water based or saline solution.

In certain embodiments, the actual signal of the subject can then be compared to the stored "signature" profiles or signals of Raman data corresponding to predetermined substances or analytes to identify the presence of one or a plurality of the selected substances and/or to estimate or quantitatively determine the concentration of that substance(s) in the subject. Thus, the present invention is able to assess, non-invasively, at physiologic levels (typically in the millimolar range, but the levels can also be in the micromolar range for certain substances), the presence of selected substances in the body of the subject. In other embodiments, a relative assessment (two or more measurements of the subject analyzed for differences or changes) may be performed, alone, or with the use of base or reference spectra. The relative assessment can include obtaining at least two different Raman spectrum signals of the subject, over time, and comparing any shift in peaks, and, thus, physiological changes, in the subject at particular frequencies.

Figure 5:
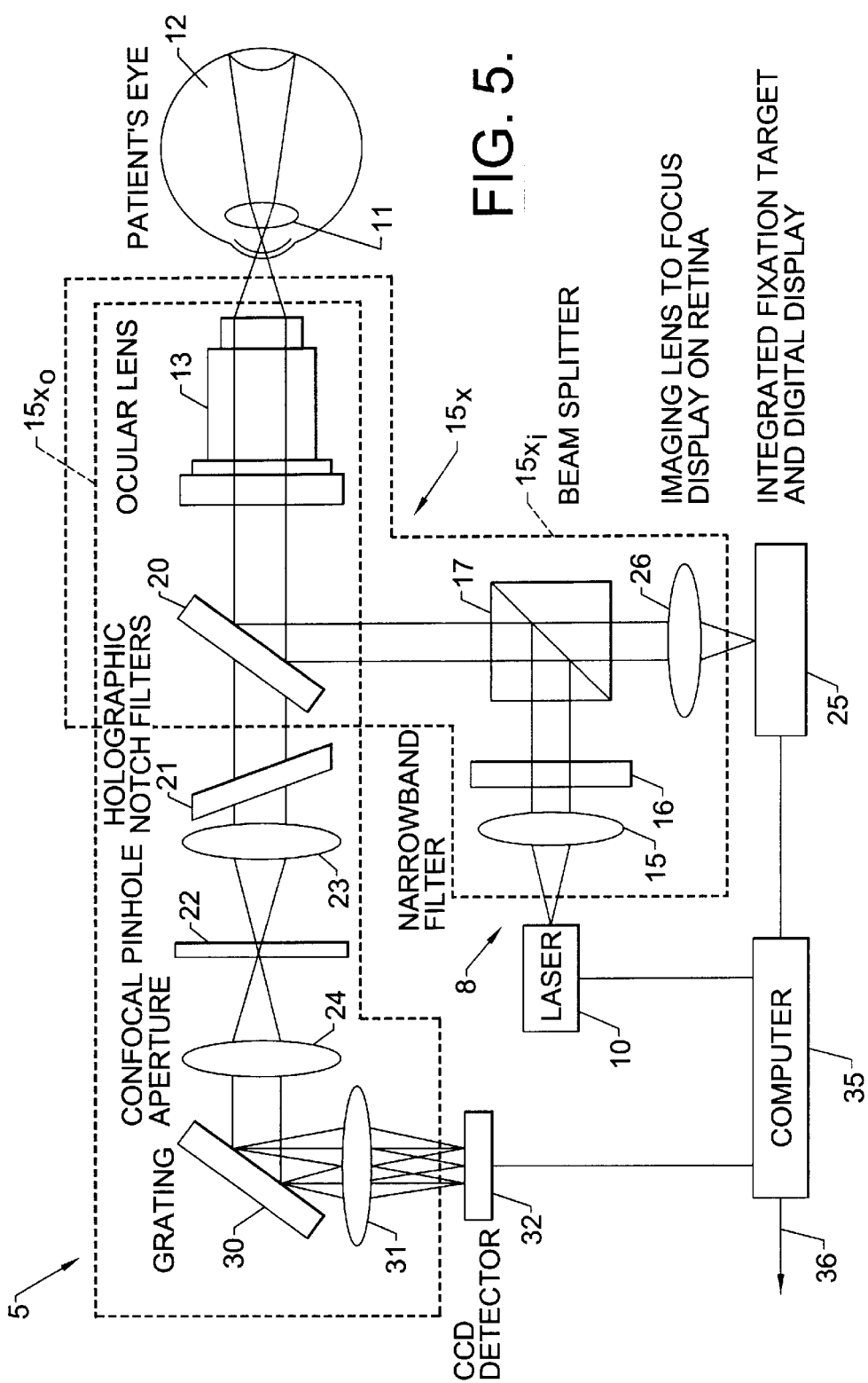
FIG. 5 schematically illustrates a first embodiment of an apparatus of the invention.
Figure 10A:
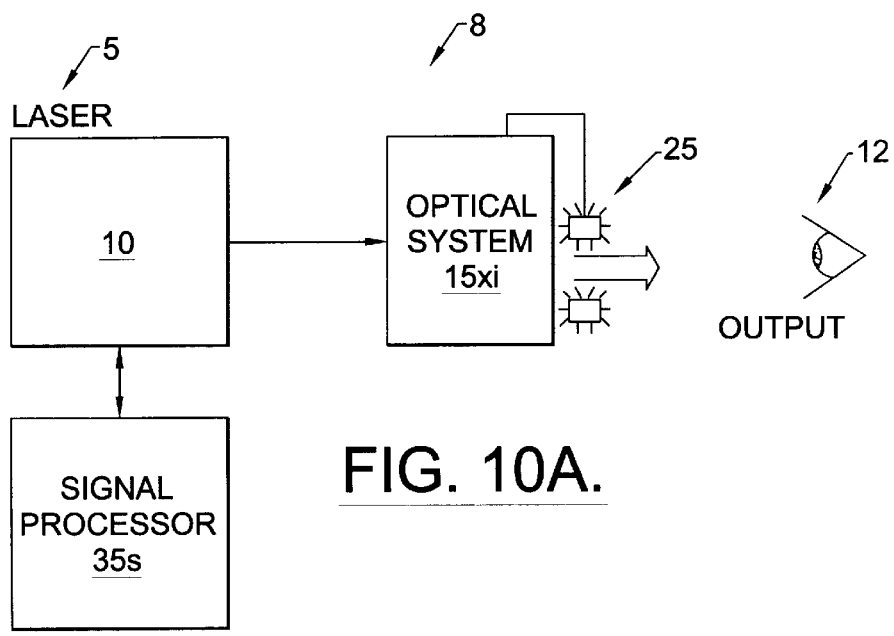
FIG. 10a is a schematic illustration of one embodiment of a light generation or light pulse system according to the present invention.

As shown in FIG. 5, in one embodiment of the present invention, the system 5 can be described has having a light (excitation or illumination) signal generation portion 8 and a detection portion 9 (FIG. 10b) with a laser 10 and an optical system 15x, along with a fixation target 25. The optical system 15x can be broken into an input portion 15xi (relays the light to the subject's eye) and an output portion 15xo (relays the reflected light from the subject). As shown in FIG. 10a, the light signal generation portion 8 includes the laser 10, a signal processor 35s, the input optical system 15xi which is configured to direct the light signal into a selected region in the eye 12 of the subject (whether the conjunctiva vessel(s), the AH, or the vitreous humor). The light generation portion 8 shown also includes a fixation target 25 used to help focus the subject's eye to the light transmission path. The target 25 may be configured to extend adjacently above, below or about the perimeter of a light exit/entrance aperture, preferably proximate to the aperture to allow the eye to focus directly at or into the aperture during operation or data acquisition.

Figure 10B:
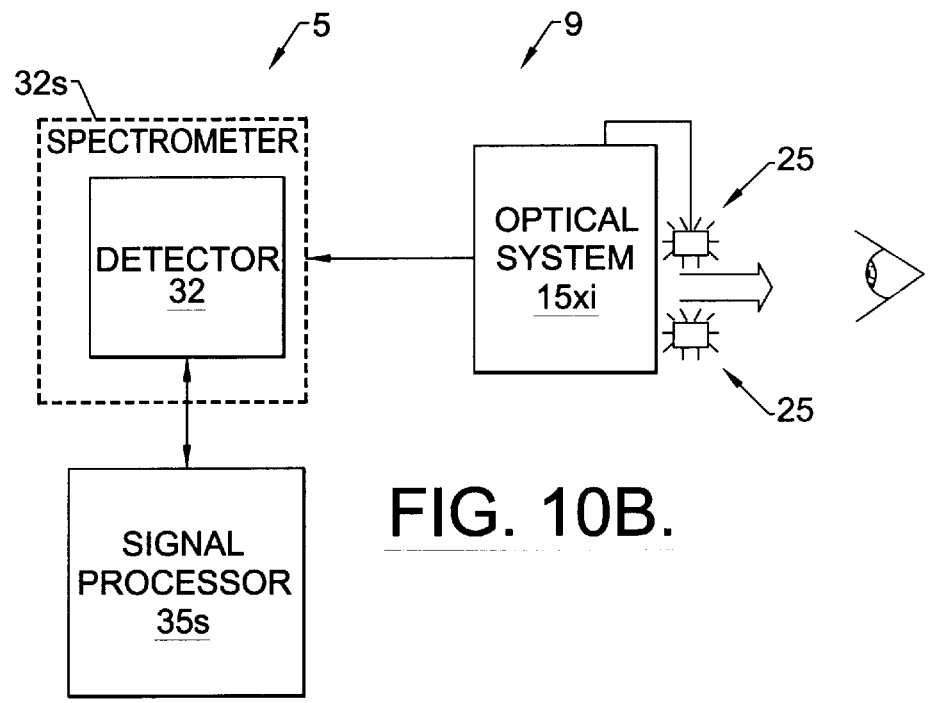
FIG. 10b is a schematic illustration of one embodiment of a detection system according to the present invention.

As shown in FIG. 10b, the system 5 also includes the detection portion 9 which receives the light as it exits the selected region of the eye and detects the Raman spectrum associated therewith. The detection portion 9 can include the output optical system 15xo (which may share some of the optical components used in the input optical system 15xi), and a spectrometer 32s with a detector 32, and a signal processor 35s. The signal processor 35s is typically the same in the transmission and detection portions 8, 9 of the system 5.

A schematic diagram of one embodiment of the system 5 is shown in FIG. 5. In certain embodiments, in operation, a tunable, narrow-band laser beam from laser 10 is focused into the anterior chamber 11 of the eye 12 through an objective or ocular lens 13 via lens 15 and filter 16, beam splitter 17, and filter 20. In certain embodiments, a non-fluorescing objective lens with suitable numerical aperture (e.g. 0.2–0.5) can be used such that Raman scattering from the selected region (i.e., the aqueous humor) is maximized while scattering from adjacent structures (e.g., lens, cornea, and iris) is reduced. The objective lens can be configured with respect to the eye so that it has adequate working distance to permit focusing of the laser into the selected region of the eye (for the AH, the middle of the anterior chamber of the eye) without direct contact with or touching of the cornea. An integrated fixation target projected from display screen 25 can be projected via lens 26 through the same objective lens as the laser, but is focused on the retina of the eye. Focusing this fixation target on the retina simultaneously can control direction and focusing of the laser light into the desired region of the eye (such as, in some embodiments, to the anterior chamber and the AH).

As shown in FIG. 5, in certain embodiments, the light collected by the objective lens is directed through holographic notch filters 20, 21 to remove the undesired portion of the reflected scattered light, such as the Raleigh scattered light. The Raman scattered light passes through these filters with minimal attenuation and is focused through a confocal pinhole aperture 22 by lenses 23, 24. The pinhole and the focal point in the eye are confocal such that light from adjacent structures in the eye can be filtered at this aperture. The pinhole 22 also serves as the entrance aperture to the spectrometer. The spectrometer shown is an imaging spectrograph with a grating 30, lens 31 and a CCD detector array 32.

A signal processor 35s, or controller which can be provided in a computer 35, controls the laser 10, the fixation target and readout display 25, and receives data from the CCD detector 32. The architecture of the spectrometer shown in the figures is merely one example of devices that are suitable for this application. Many types of spectrographs can be utilized including Fourier transform spectrographs, spectrographs using liquid crystal tunable filters or other tunable elements. Information can be transmitted to a remote source such as a computer, database, remote physician or the like via modem or other connection through a suitable communication link 36 via a wireless link or a computer network such including an intranet or a global computer network link such as an internet link (such as the world wide web), etc.

In certain embodiments, the CCD detector 32 in the spectrometer is of a red-shifted, back-thinned, thick epitaxial design such that its sensitivity is optimal in the 700–1100 nanometer spectral region. Other types of suitably sensitive detectors may be suitable as well.

As noted above, a signal processor 32s such as a digital signal processor in a general purpose or special purpose computer processes the output of the detector 32. The signal processor or computer or other controller can control the laser beam frequency and the power or intensity of the laser pulse from the laser source 10.

In some embodiments, the signal processor 32s, computer, or controller can switch the frequency of the laser to permit subtraction of fluorescence as described previously. The signal processor or computer can also direct information to a digital display imaged onto the retina. The patient can then read the results of the analysis on this display. For certain embodiments, the results can be displayed on the exterior of the device so that a clinician or police officer (the latter being particularly directed for narcotics or blood alcohol evaluations) can easily read same. Further, the data or results can be date and time coded and digitally stored and printed as a medical or police record.

Figure 6:
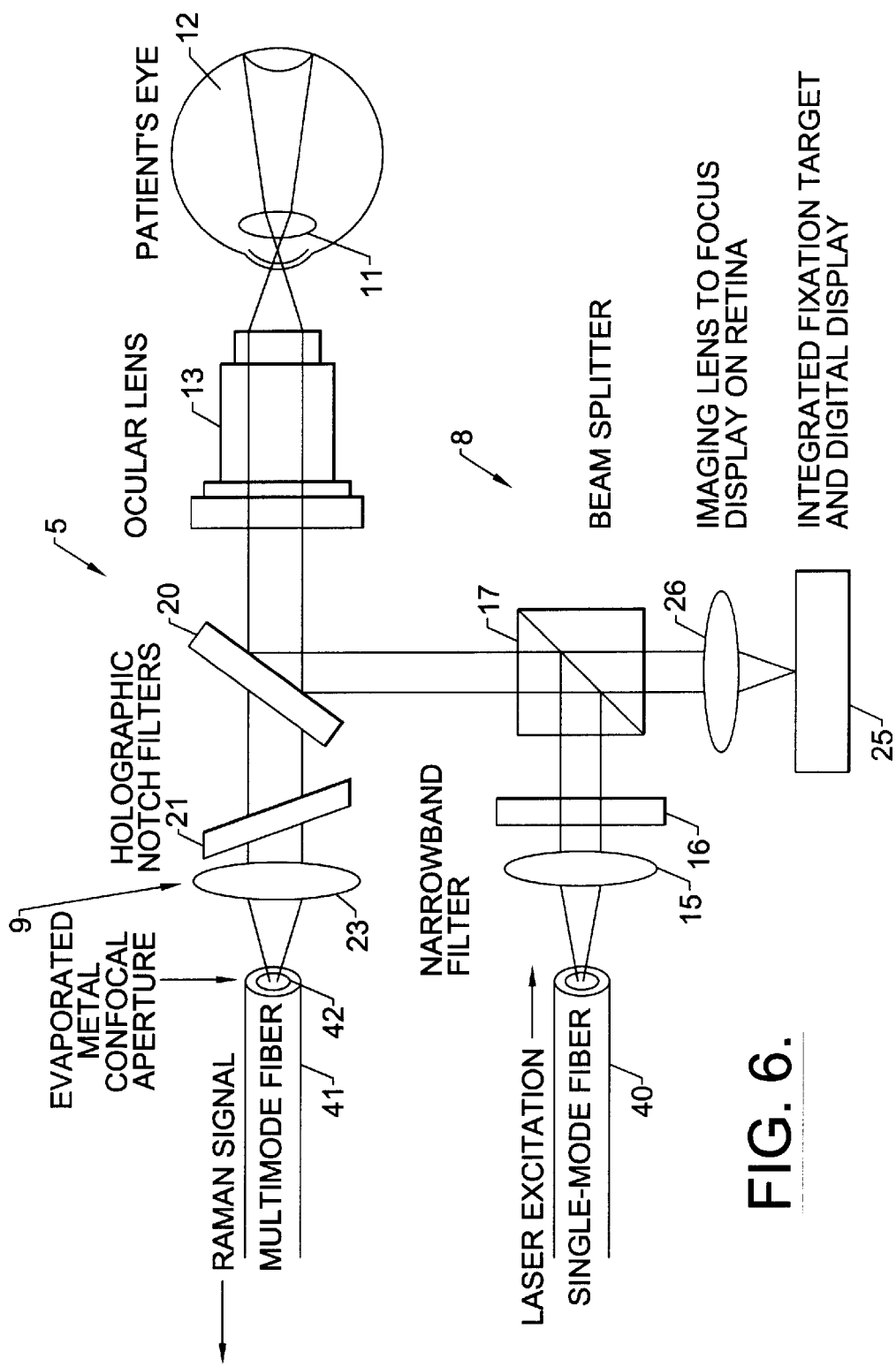
FIG. 6 schematically illustrates a second embodiment of an apparatus of the invention.

As shown in FIG. 6, fibers 40, 41 may be used to deliver the laser beam and collect the Raman scattered light. In certain embodiments, the confocal aperture is a circular aperture 42 placed on the end of a multimode fiber. As with the pinhole aperture shown in FIG. 5, the end of the fiber can be placed so that it is confocal with the objective lens' focal point in the anterior chamber of the eye. A single mode fiber can be used to direct the laser beam into the anterior chamber of the eye. This single mode fiber can help facilitate a diffraction limited spot size at the focal point of the objective.

A fiber delivery and collection system like that depicted in FIG. 6 can be connected to alternative detection systems, one of which is shown in FIGS. 7a–b. This alternative detection system can allow for subtraction of the fluorescence spectrum as well as selected sampling of the frequencies most important for calculation of glucose concentration. Such an alternative detection system may decrease the size and cost of the instrument. The system depicted in FIG. 7 uses one or more fixed frequency or tunable lasers to illuminate the aqueous humor of the eye using the optical delivery system shown in FIG. 6.

FIG. 7a illustrates that each spectral feature 50a, 50b, 50c of the Raman scattered light is related to the excitation wavelength by a fixed offset, usually expressed in wavenumbers. Changing the excitation wavelength causes the Raman spectra to shift in wavelength, as depicted by the different feature or portion of the signal, captured in detector range window $\Delta_\lambda$ 51 (a relatively narrow band of the signal such as about 10 nm) based on Raman spectra 52 for excitation frequency $L_{\lambda 1}$ as compared to Raman spectra 53 for excitation frequency $L_{\lambda 2}$.

An apparatus that takes advantage of the foregoing is schematically illustrated in FIG. 7b. Like components to FIGS. 5 and 6 are assigned like numbers. Laser drivers and/or tuning electronics 60 are operatively associated with a tunable laser or a plurality of fixed wavelength lasers 61, 62, 63. A series of one or more bandpass filter/detector elements 65, 66, 67 operatively associated with amplifiers and an analog to digital converter 68 is used to sample the spectrum of the collected light. The center wavelength and bandwidth of each filter may be chosen to correspond with a different Raman spectral peak of aqueous humor important for quantification of the selected substance (such as alcohol, an illegal narcotic or banned substance, a poison, or glucose). If this laser is tunable over about a nanometer or so, subtraction of the fluorescent components of the acquired spectrum may be possible as discussed earlier. Using a laser with a wider tuning range can allow the Raman shifted spectra to be scanned or slid across a smaller number of bandpass filter/detectors. Since semiconductor lasers with extremely wide tuning ranges are not commercially readily available, one may instead use a set of narrowly tunable lasers each with a different center wavelength as the laser means in conjunction with a series of bandpass filter/ detectors for this purpose. Other suitable light sources can also be used.

Advantageously, the systems described herein may be configured so that optical components need not and do not contact the cornea of the eye during use, which many patients find objectionable (e.g., by providing a suitable monocular eye cup for contacting the orbit around the eye).

The apparatus of the invention can be implemented as a spectrometer base unit attached by a fiberoptic cable to an ocular probe, or as a single integrated unit including foreoptics, spectrometer, detector, computer and display. The apparatus can be configured as a relatively lightweight and portable device. In some embodiments, the optics and laser source can all be configured to be held in a housing which can be mounted on the user as a headset, or on a portable platform device similar to vision screening or vision correction devices used during vision exams.

Figure 8:
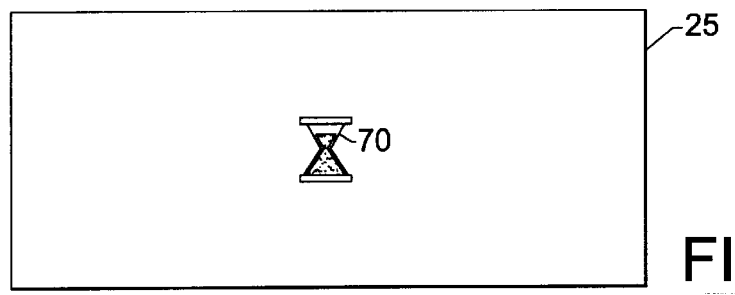
FIG. 8 illustrates a visual fixation display that can be utilized in an apparatus of the invention.

As noted above, a visual fixation target such as a mirror, LED, or display such as an active liquid crystal matrix display or the like can be built into the optical apparatus such that it is held in the housing in visual communication with the patient or user during operation to facilitate focusing of the excitation light into the anterior chamber and maintain stability of the eye (so that it is properly aligned with the eye of the subject). In the embodiment of FIGS. 5–7, a display screen such as a liquid crystal display is employed. As shown in FIG. 8, a blinking fixation target in the form of an hourglass 70 can be displayed, focused on the retina, during acquisition of the spectra by the apparatus. Other fixation target forms can also be used such as text, letters, numbers, or other recognizable shapes or objects. This can help optimize the Raman signal from the aqueous humor and reduce light exposure to other structures of the eye. The fixation target can be active during the time that the laser beam is active and illuminating the subject's eye.

Figure 9:
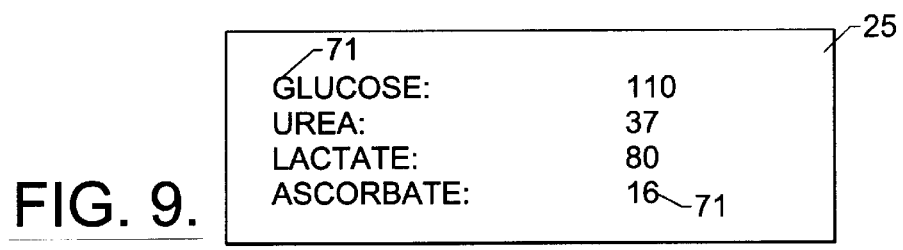
FIG. 9 illustrates a visible readout display that can be utilized in an apparatus of the invention.

As shown in FIG. 9, in some embodiments, a visible indication of the results of the test in the form of alphanumeric indicia 71 (or other suitable form, such as a graphical display) can be displayed on the same screen immediately after the acquisition step (or to a remote or externally visible screen for other embodiments). The indicia of FIG. 9 provides a readout for all of the principal Raman-active compounds of the aqueous humor, but the display can be of a targeted compound of interest (filtered from the overall spectra) corresponding to one or more, of a desired concentration level of a selected substance (such as alcohol) as desired.

In some embodiments, a motion sensor can be incorporated into the device so that the test can be aborted upon movement of the eye away from the focal point or so that a clinician is alerted as to the movement. For example, upon transmission of the laser pulse to the selected region in the eye, a sensor can be concurrently operated and used to detect movement of the retina away from the target focal point.

The excitation laser light source can be any suitable laser beam source which can generate a suitable laser beam signal at a desired frequency output. A distributed feedback laser can be used to reduce instrument size. Tunable or multiple fixed frequency lasers can be combined with bandpass filters (Puppels et al., *Applied Spectroscopy* 47, 1256–67 (1993)) that can generate pulses for Raman scattering at wavelengths that provide optimum information for multivariate analysis (this can reduce the cost and size of the instrument compared to the use of holographic filters or gratings).

The laser beam can be pulsed from the generator or from the optical system to provide the desired length and power or energy to the tissue in the eye. The power of the excitation laser beam pulse should be sufficiently low to avoid tissue toxicity, but sufficiently high to provide a measurable Raman signal from the aqueous humor. In general, the laser beam pulse will be at a wavelength of from 600 to 900 nanometers. In some embodiments, the laser wavelength can be a wavelength of 780 to 860 nanometers to reduce fluorescence, increase tissue penetration, and reduce phototoxicity to the eye. In other embodiments, the wavelength can be generated at a lower wavelength, such as between 600–700 nanometers, so as to increase the signal to noise ratio of the signal and/or to decrease the power level of the signal in the eye.

The duration of the pulse will typically be from 1 to 60 seconds in length, and typically be from about 5–20 seconds long.

The total energy of the laser pulse transmitted to the eye will typically be between 70–500 milliJoules, with instantaneous power preferably not exceeding about 30–50 milliWatts. The optical components of the apparatus used to carry out the method are preferably configured so that energy on the retina of the eye (as well as other areas susceptible to tissue toxicity, such as the lens and cornea) transmitted from the excitation laser beam pulse is not greater than 3000 mW/cm$^2$, more preferably not greater than 1000–2000 mW/cm$^2$, and even more preferably, below about 500 mW/cm$^2$.

In certain embodiments, a low energy excitation wave can be used to generate the Raman signal spectrum. "Low energy", as used herein, means power which is on the order of about 10–400 mJ or less, and typically between about 70–330 mJ. The energy exposure will depend on the power and pulse length of the excitation pulse. Longer wavelength pulses (i.e., above 700 nm) may be used, typically with energy closer to the higher end of the scale, while lower wavelengths (600–700 nm) may be able to employ lower energy exposure levels. In one embodiment, a wavelength of about 633 nm can be used for a pulse of about 5–10 seconds corresponding to about a 2 mW power exposure level and between a 10–20 mJ energy exposure to the patient's eye for each measurement or monitoring signal obtained. In other embodiments, an optical excitation pulse may have a 785 nm wavelength (or other suitable wavelength), and a pulse length of about 20 ms and a power rating of about 15 mW. In another embodiment, a 5 sec, 16 mW pulse (having a energy exposure level of about 75 mJ) can be used to obtain the in vivo reading of a substance such as a cancer treatment agent in the selected region of the eye (typically the AH).

For multiple measurements, the devices may be able to be configured to focus on a different eye, alternating the eye to which the light is transmitted, to reduce the amount of exposure to any one eye.

In certain embodiments, the chemical or analyte concentration in the blood can be measured within a 90–99% accuracy level as determined by extracting the aqueous humor, putting it in a test tube and measuring the Raman spectrum. The band of interest is typically in the 200–3200 cm-1 band.

Any suitable detector 32 can be used to detect a Raman spectrum from illuminated aqueous humor. In certain embodiments, a CCD detector or CCD camera can be used to detect reflective light as they may exhibit increased sensitivity over other types of detectors. The CCD detector preferably is configured to have high quantum efficiency in the near infrared range. The high quantum efficiency may be achieved by any suitable means, such as employing a back thinned detector, but one sufficiently thick to reduce etalon effect.

The devices of the invention can be operatively associated with a patient's medical equipment such as an insulin pump (for D-glucose) or to a dialysis machine (for urea) by wireless or wired electrical or fiber optic lines, radio frequency transmitters and receivers or the like to provide information on the appropriate analyte that can then be used to control that equipment. For example, the reading can be used to automatically activate or increase or decrease the output of the equipment such as the insulin pump in response to blood glucose levels, or to regulate the dialysis machine.

In telemedicine applications, the instrument of the invention can be conveniently operatively associated with a remote read-out terminal through a communication link such as a telephone, cable, computer, modem, intranet, internet connection or other communication line with any suitable relay or interconnection means (such as an electrical or fiber optic lines, radio frequency transmitters and receivers, etc.) to provide information on the blood or intracranial (blood-brain fluid) analyte to a remote physician or medical provider (e.g., through a telephone, cable, or wireless connection to a direct security (for in-home parole) or medical monitoring agency or to a selected destination on the intranet, internet, or world wide web).

Figure 11:
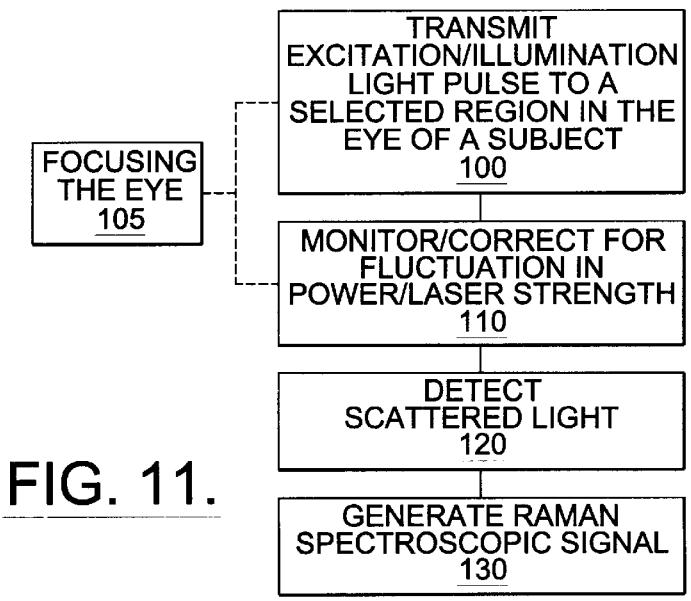
FIG. 11 is a block diagram of a method for determining the presence or the blood level concentration of a selected analyte according to certain embodiments of the present invention.

FIG. 11 illustrates method steps for obtaining spectrographic readings of the selected region of the eye of a subject according to certain embodiments of the present invention. As shown, an excitation or illumination light pulse is transmitted to the selected region of the eye of the subject (Block 100). In certain embodiments, this can be carried out by positioning a mask-like device over the eyes of the subject (similar to that used in eye exams) so that (a) the housing of the device aligns over the eye socket(s) to seal the eye(s) from ambient lighting, (b) the excitation pulse light is efficiently directed into the eye (without scattering into the environment), (c) and the light reflected from the eye (such as the AH) can be captured, but no physical contact with the cornea of the eye itself is required. For example, a monocular eye cup (or binocular eye cups) can be used to contact the orbit around the eye and yet space the optical components from contacting the cornea. The scattered light from the illumination light pulse is then detected (Block 120).

During the transmission and detection steps, the eye can be focused to a desired location or target spot (Block 105) to help direct the excitation light out of and into the eye in a repeatable and reliable manner (to define a consistent transmission path so that the reflected light is attributed to proper and reliable illumination of the VH, AH, or conjunctiva vessel(s)). In so doing, a manual or autofocusing technique can be used. For manual focusing, various methods can be used to allow the user to adjust the focus. For example, a pinwheel can be turned clockwise or counterclockwise to focus on an object or text or other visual fixation target to be displayed in the device (typically the object or text is displayed in a miniaturized display (such as an active matrix display) positioned about the opening through which the light is transmitted proximate the light transmission path). For example, LED's or active matrix displays can be used to generate text or a blinking or continuous light, which attracts the visual attention of the subject and which the subject watches or reads during the transmission and detecting steps.

Similarly, for autofocusing, the subject can look to the visual fixation target mounted in the device in visual communication with the eye. The presentation of the object can be automatically stepped through a visual protocol which can magnify or adjust the visual presentation until the subject can read or recognize the object. When this happens, the reading or recognition indicates that the focus is sufficient, and the reading can be taken (i.e., the transmission and detection of light). Autofocusing systems with corrected optic systems are well known to those of skill in the art. For example, optic systems similar to those used to assess vision and determine a suitable lens correction for a subject during vision examinations can be incorporated into the devices according to embodiments of the present invention. Although a contact lens may remain in place during the reading, it is preferred that glasses or other objects which may physically interfere with the mounting of the device over the eyes, be removed during the test.

The power or beam strength of the light pulse can be monitored so that fluctuation in the power or strength of the light beam which is transmitted to the user can be adjusted so that it the current and/or heat is regulated to be substantially constant (constant current or heat) or numerically corrected for, typically in the signal processor 35s (Block 110). A Raman spectrum of the targeted region of the eye can then be generated based on the detected and corrected light spectroscopic signal (Block 130). Typically, well-known statistical correlation or normalization techniques are used to generate the Raman spectrum from the scattered light data received at the detector. See e.g., *Standard Practices for Infrared, Multivariate, Quantitative Analysis*, ASTM E 1655-97; Beebe et al., *An Introduction to Multivariate Calibration and Analysis*, Anal. Chem. 59, 1007A–10017A (1987); Draper et al., *Applied Regression Analysis* (2d ed., John Wiley and Sons, 1981); Maliowski et al., *Factor Analysis in Chemistry* (2d ed., John Wiley and Sons, 1991); Mark, H., *Principles and Practice of Spectroscopic Calibration* (John Wiley and Sons, 1991); Martens et al., *Multivariate Calibration* (John Wiley and Sons, 1989); and McClure, G., Ed., *Computerized Quantitative Infrared Analysis*, ASTM STP 934, ASTM (Philadelphia, 1987). The contents of these references are hereby incorporated by reference as if recited in full herein.

Thus, any number of suitable computational analysis may be used including linear (e.g., algebraic or least squares/ partial least squares) or nonlinear (e.g., artificial neural networks) multivariate analysis techniques, such as, multiple linear regression (MLR), classical least-squares (CLS, K-matrix), inverse-least-squares (ILS, P-matrix), principal component regression (PCR, PCA, factor analysis), and partial least-squares in latent variables (PbS). See Schulze et al., *Artificial neural network and classical least squares methods for neurotransmitter mixture analysis*, Jnl. Neuroscience Methods 56(2); 155–167 (February 1995); and Wang et al., *Analysis of metabolites in aqueous solutions by using laser Raman spectroscopy*, Applied Optics, 32(6); 925–9 (February 1993). See also Brown, C. W., *Classical and Inverse Least-Squares Methods in Quantitative Spectral Analysis*, Spectrosc., 1; 23–37 (1986); Brown, et al., "Matrix Representations and Criteria for Selecting Analytical Wavelengths for Multicomponent Spectroscopic Analysis", Anal. Chem. 54; 1472–1479 (1982); Carey et al., *Multicomponent Analysis using an Array of Piezoelectric Crystal Sensors*, Anal. Chem., 59; 1529–1534 (1987); Haaland, D. M. *Classical versus Inverse Least-Squares Methods in Quantitative Spectral Analyses*, Spectrosc. 2; 56–57 (1987); Haaland et al. *Application of New Least-squares Methods for the Quantitative Infrared Analysis of Multicomponent Samples*, Appl. Spec., 36; 665–673 (1982); Haaland et al., *Improved Sensitivity of Infrared Spectroscopy by the Application of Least Squares Methods*, Appl. Spec. 34; 539–548 (1980); Haaland et al. *Multivariate Least-Squares Methods Applied to the Quantitative Spectral Analysis of Multicomponent Samples*, Appl. Spec., 39; 73–84 (1985); Kargacin et al. *Ion Intensity and Image Resolution in Secondary Ion Mass Spectrometry*, Anal. Chem. 58; 2300–2306 (1986); Kisner et al. *Multiple Analytical Frequencies and Standards for the Least-Squares Spectrometric Analysis of Serum Lipids*, Anal. Chem., 55; 1703–1707 (1983); Kisner et al., *Simultaneous Determination of Triglycerides, Phospholipids, and Cholesteryl Esters by Infrared Spectrometry*, Anal. Chem., 54; 1479–1485 (1982); Lam, R. B. *On the Relationship of Least Squares to Cross-correlation Quantitative Spectral Analysis*, Appl. Spec., 37; 567–569 (1983); Maris et al., *Nonlinear Multicomponent Analysis by Infrared Spectrophotornetry*, Anal. Chem., 55; 1694–1703 (1983); McClure, G. L. et al. *Application of Computerized Quantitative Infrared Spectroscopy to the Determination of the Principal Lipids Found in Blood Serum*, Computerized Quantitative Infrared Analysis, ASTM STP 934, G. L; McClure, Ed. American Society for Testing and Materials, Philadelphia, 13; 1–154 (1987); Otto, M. et al. *Spectrophotometric Multicomponent Analysis Applied to Trace Metal Determinations*, Anal. Chem., 57; 63–69 (1985); Antoon et al. *Factor Analysis Applied to Fourier Transform Infrared Spectra*, Appl. Spec., 33; 351–357 (1979); Are et al., *On the Effect of Calibration and the Accuracy of NIR Spectroscopy with High Levels of Noise in the Reference Value*, Appl. Spec. 45; 109–115 (1991); Bulmer et al. *Factor Analysis as a Complement to Band Resolution Techniques. I. The Method and its Application to Self-Association of Acetic Acid*, J. Phys. Chem. 77; 256–262 (1973); Culler et al. Factor Analysis Applied to a Silane Coupling Agent on E-Glass Fiber System", Appl. Spec., 38; 495–500 (1984); Dale et al., *Principal Component Analysis of diffuse Near-Infrared Reflectance Data From Paper Currency*, Appl. Spec., 43; 1399–1405 (1989); Gillette et al., *Noise Reduction via Factor Analysis in FT-Ir Spectra*, Appl. Spec., 36; 535–539 (1982); Kargacin et al. *Ion Intensity and Image Resolution in Secondary Ion Mass Spectrometry*, Anal. Chem., 58; 2300–2306 (1986); Lindberg et al., *Partial Least Squares Method for Spectrofluorimetric Analysis of Mixtures of Humic Acid and Ligninsulfonate*, Anal. Chem., 55; 643–648 (1983); Lukco et al., *The Use of GC-AES Multielement Simulated Distillation for Petroleum Product Fingerprinting*, J. Chrom. Sci. March, 1993; Malinowski et al. Factor Analysis in Chemistry, 2nd edition, John Wiley and Sons, New York, 1991; Malinowski, E. R., *Theory of the Distribution of Error Eigenvalues Resulting from Principal Component Analysis with Applications to Spectroscopic Data*, J. Chemo., 1; 33–40 (1987); Malinowski, E. R., *Statistical F-Tests for Abstract Factor Analysis and Target Testing*, J. Chemo., 1; 49–60 (1987); Malinowski, E. R. *Theory of Error in Factor Analysis*, Anal. Chem., 49; 606–612 (1977); Malinowski, E. R., *Determination of the Number of Factors and the Experimental Error in a Data Matrix*, Anal. Chem., 49; 612–617 (1977); Naes et al., *Selection of Samples for Calibration in Near-Infrared Spectroscopy. Part I: General Principles Illustrated by Example*, Appl. Spec. 43; 328–335 (1989); Rao et al., *Factor Analysis and Least-Squares Curve-Fitting of Infrared Spectra: An Application to the Study of Phase Transitions in Organic Molecules*, Appl. Spec., 38; 795–803 (1984); Schostack et al., *Preferred Set Selection by Iterative Key Set Factor Analysis*, Chemo. and Intel. Lab. Sys., 6; 21–29 (1989); Vaughan et al., *Determination of Ni by ICP-MS. Correction of Oxide and Hydroxide Interferences Using Principal Components Analysis*, Appl. Spec., 44; 1685–1689 (1990); Carey et al., *Multicomponent Analysis using an Array of Piezoelectric Crystal Sensors*, Anal. Chem., 59; 1529–1534 (1987); Donahue et al., *Analysis of Deoxvribonucleotides with Principal Component and Partial Least-Squares Regression of UV Spectra after Fourier Processing*, Appl. Spec., 44; 407–413 (1990); Geladi et al., *Partial Least-Squares Regression: A Tutorial*, Anal. Chim. Acra, 185; 1–17 (1986); Haaland et al., *Partial Least-Squares Methods for Spectral Analysis 1. Relation to Other Quantitative Calibration Methods and the Extraction of Qualitative Information*, Anal. Chem., 60; 1193–1202 (1988); Haaland et al., *Partial Least-Squares Methods for Spectral Analysis 2. Application to Simulated and Glass Spectral Data*, Anal. Chem., 60; 1202–1208 (1988); Hanna et al., *A Comparison of Methods Used for the Reconstruction of GC/FT-17R Chromatograms*, J. Chrom. Sci., 17; 423–427 (1979); Kelly et al., *Prediction of Gasoline Octane Numbers from Near-infrared Spectral Features in the range 660–121 5 nm*, Anal. Chem., 61; 313–320 (1989); Lindberg et al., *Partial Least-Squares Method for Spectrofluorimetric Analysis of Mixtures of Humic Acid and Ligninsulfonate*, Anal. Chem., 55; 643–648 (1983); and Otto et al., *Spectrophotometric Multicomponent Analysis Applied to Trace Metal Determinations*, Anal. Chem., 57; 63–69 (1985). The contents of these references are hereby incorporated by reference as if recited in full herein.

Figure 10C:
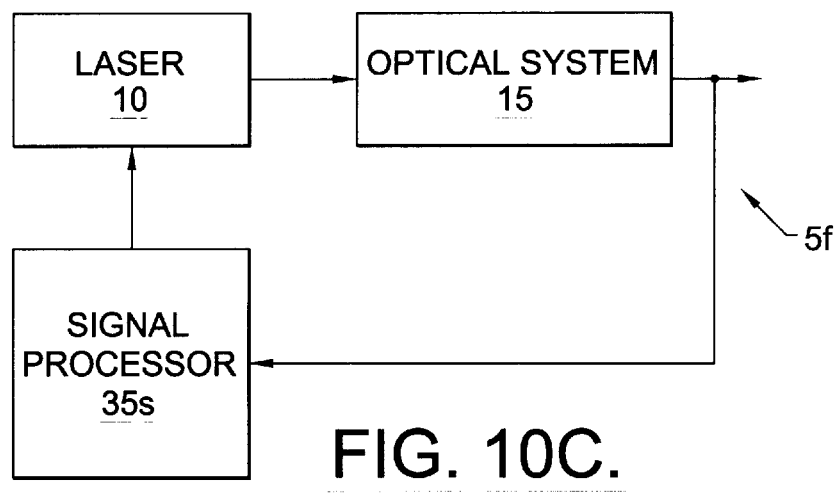
FIG. 10c is a schematic of one embodiment of a system with a closed loop feedback control system according to the present invention.

FIG. 10C illustrates that the device 5 may include a closed loop feedback system 5f for monitoring and regulating the strength or intensity of the light excitation beam output to the eye of the subject. The feedback system 5f may employ a beam splitter positioned to bleed off a portion of the beam at a location which is proximate to the aperture (the beam outlet port) and substantially continuously detect the beam power, intensity, or energy associated therewith to monitor the power of the excitation beam as it is transmitted out of the device. Other embodiments can include dynamically monitoring the current or power load of the laser 10 to adjust for temperature or other operational drift or power fluctuation during operation. The signal processor 35s can then adjust the input to the laser as needed and/or store the excitation beam data so that the Raman spectrum can be adjusted to reflect the actual beam energy or power transmitted to the user.

Figure 10D:
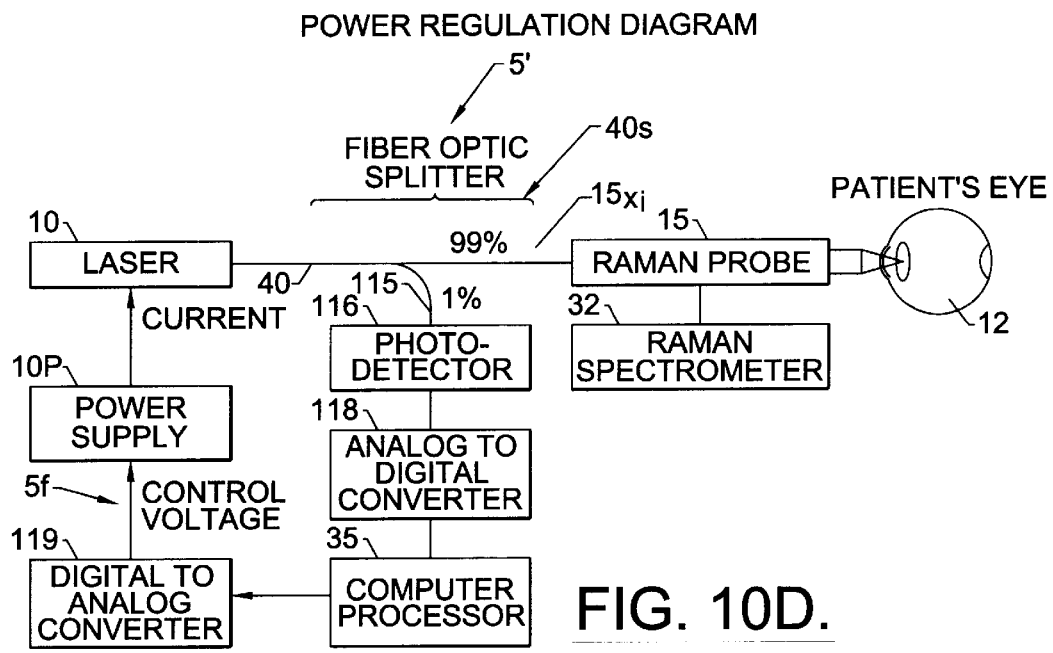
FIG. 10d is a schematic of an alternate closed loop feedback system according to embodiments of the present invention.

FIG. 10D illustrates one operational embodiment of a device with power regulation according to the present invention. As shown, the laser 10 is operably associated with a power supply 10p. The laser 10 directs the light through a fiber optic cable 40 which includes or is coupled to a fiber optic splitter 40s which directs or bleeds a small portion of the light away from the primary light transmission path (and into the eye of the patient). A substantial portion of the light remains in the primary light transmission path and is directed into the Raman probe head 15 probe which can, in operation, be positioned adjacent the eye 12 of the patient. The Raman spectrometer 32 can be positioned in communication with the Raman probe so as to be able to detect the light upon its return (in the return path).

As shown, the splitter 40s may split about 1% of the excitation light away from the primary beam to a detection path 115 and into a photodetector 116 (or other suitable sensor). The photodetector 116 is in electrical communication with an A/D (analog to digital) converter 118, which converts the corresponding electrical signal so that it can be digitally input into the processor 35. Thus, the voltage or current from the photodetector 116 is measured and digitized (preferably in a substantially continuous or continuous manner during operation of the device) and the information transmitted to the processor 35 (typically a computer). The computer or processor 35 can then measure the laser power and computationally determine a new adjusted current (or voltage) to adjust the laser 10 output to the desired or target output value such that it is able to be held to within about 95% of the target output strength. In certain embodiments, the output signal strength can be held substantially constant such as within at least about 98–99%. The computer output can be converted back into analog form via a D/A converter 119 which is used to regulate the voltage power supply 10p which, in turn, regulates the input to the laser 10.

The optical system 15xi may also be configured to transmit the excitation beam such that it presents a wider cone to focus to the retina in a manner which is able to cover a larger area of the selected region in the eye to thereby operate with a lower energy/area ratio (such as, for at least some AH applications, configuring the optical system such that the numerical apertures of the input optic system 15xi is substantially matched to the output optic system 15xo (or spectrometer). In certain embodiments, a numerical aperture of about 0.2–0.5 can be used. The graph in FIG. 20C shows a sample power density and exposed retinal area for a numerical aperture of 0.25 and a 10x objective (Point A) and a larger numerical aperture of about a 0.4 (23.6 degrees for a 20x objective) at Point B.

FIGS. 20A–20C illustrate optical power density calculations performed using a canonical model of the adult eye of a human (FIG. 20A). Typically, optical toxicity power limitations for the eye are established by regulatory agencies.

Figure 15:
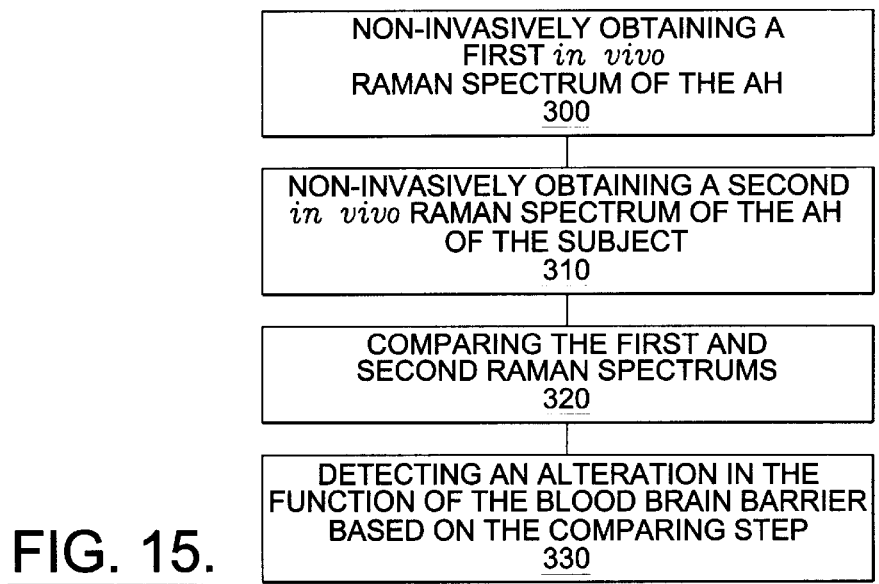
FIG. 15 is a block diagram of a method for detecting an alteration of the function of the blood brain barrier according to certain embodiments of the present invention.

FIG. 20A shows a diagram of the adult eye exposed to light through an eyepiece with a corresponding objective and numerical aperture. Marginal rays from this eyepiece are shown focusing through the cornea and into the aqueous humor within the anterior chamber. The confocal optical configuration of the instrument allows it to sample Raman scattered light in the region near the focal spot (and substantially isolated to that region). Thus, in certain embodiments, the optic design can be such that scattering from the cornea or the intraocular lens can be reduced and can be confocally blocked from the instrument's fiber-optic entrance aperture within the optical probehead (FIG. 10d, 15 probe).

FIG. 20A also shows the nodepoint (N) originally derived by Gullstrand. Gullstrand used special instrumentation to observe Purkinje reflections from both sides of the cornea and lens to develop a simple eye model which lumped the power of the cornea and the intraocular lens into a single equivalent lens with node point (N). Based on the knowledge of the position of node point (N) relative to the retina, one can calculate sizes of objects on the retinal surface. This information can be used to compute the surface area of the retina exposed by the numerical aperture (NA) (such as NA=0.25 or NA=0.4 according to certain embodiments of the design of the device and the associated eyepiece).

In this model, rays passing through (N) can be treated as if they are unrefracted as they travel through the eye and onto the retina. One can construct rays that pass through (N) but are also collinear with the eyepieces marginal rays as shown. A pair of collinear rays entering the lens equivalent model should focus on the retina. Going through this exercise with both pairs of marginal rays of the eyepiece shows that one can treat the incident beam as a point source which emanates from (N) at an angle θi, the same angle as the marginal rays make with the optical axis.

As shown in FIG. 20B, simple calculus can be employed to derive an expression for the surface area of a sphere over a solid angle delineated by θc, the angle of a ray from normal that extends to the margins of the surface area exposed on the sphere. The expression for surface area is given by equation 1.

$$A = 2\pi R^2 (1 - \cos \theta_c) \qquad \text{Equation 1}$$

θi is given (calculated as $\sin^{-1}$ of NA of the eyepiece) and not θc, an expression can be derived which relates these as a function of the radius of the globe and the relative position of N given by $x_0$. As shown by equation 2 in FIG. 20B, trigonometry can be used to derive this relationship. For any θi, equation 2 can be solved numerically for θc, using the Newton-Rapson method.

$$R \sin \theta_c = (R \cos \theta_c + x_0) \tan \theta_i \qquad \text{Equation 2}$$

FIG. 20C is a graph which plots exposed retinal surface area (right vertical axis) and power density assuming a 30 mW illumination (on the left vertical axis) on the retina as a function of various eyepiece designs defined by the angle of incidence "θi". The line indicated at the angle of incidence just below 15 degrees (Point A) corresponds to the numerical aperture 0.25 used for obtaining certain of the experimental data shown or described herein. The angle of incidence associated with a numerical aperture of 0.4 is at about 23.6 degrees (larger exposed retina area and lower power density), shown at Point B, used to obtain the data illustrated in FIGS. 21A–C. This angle can also be expressed in terms of NA or "f"-number (the focal length divided of the fully illuminated diameter of the limiting aperture). The numerical aperture of the entire system places an upper bound on the effective numerical aperture. For example, the numerical aperture of the embodiment of the device 5 of the spectrometer used to determine certain of the described results is f/1.8 (NA=0.267). However, the fiber optic cable between the spectrometer and the probe head, limits the numerical aperture to f/2.0 (NA=0.24). Thus using an objective at a higher f number than the fiber is counterproductive since Raman scattered light at the outer angles is not captured by the fiber. Using the instrument with the same incident power but with an objective with an f number smaller than f/2 will generally result in higher power densities on the retina with no increase in Raman signal gain. This is because maximum collection efficiency is achieved at a particular by matching the f number of the eyepiece to that of the system. The present invention can provide designs which can be considered close to optimal, by configuring the system with an f number which is approximately equal to the eyepiece numerical aperture. Using 30 mW of illumination, one embodiment can provide a lens configuration which exposes about 0.58 cm$^2$ of the retina to a power density of about 51.5 mW/cm$^2$.

Figure 18:
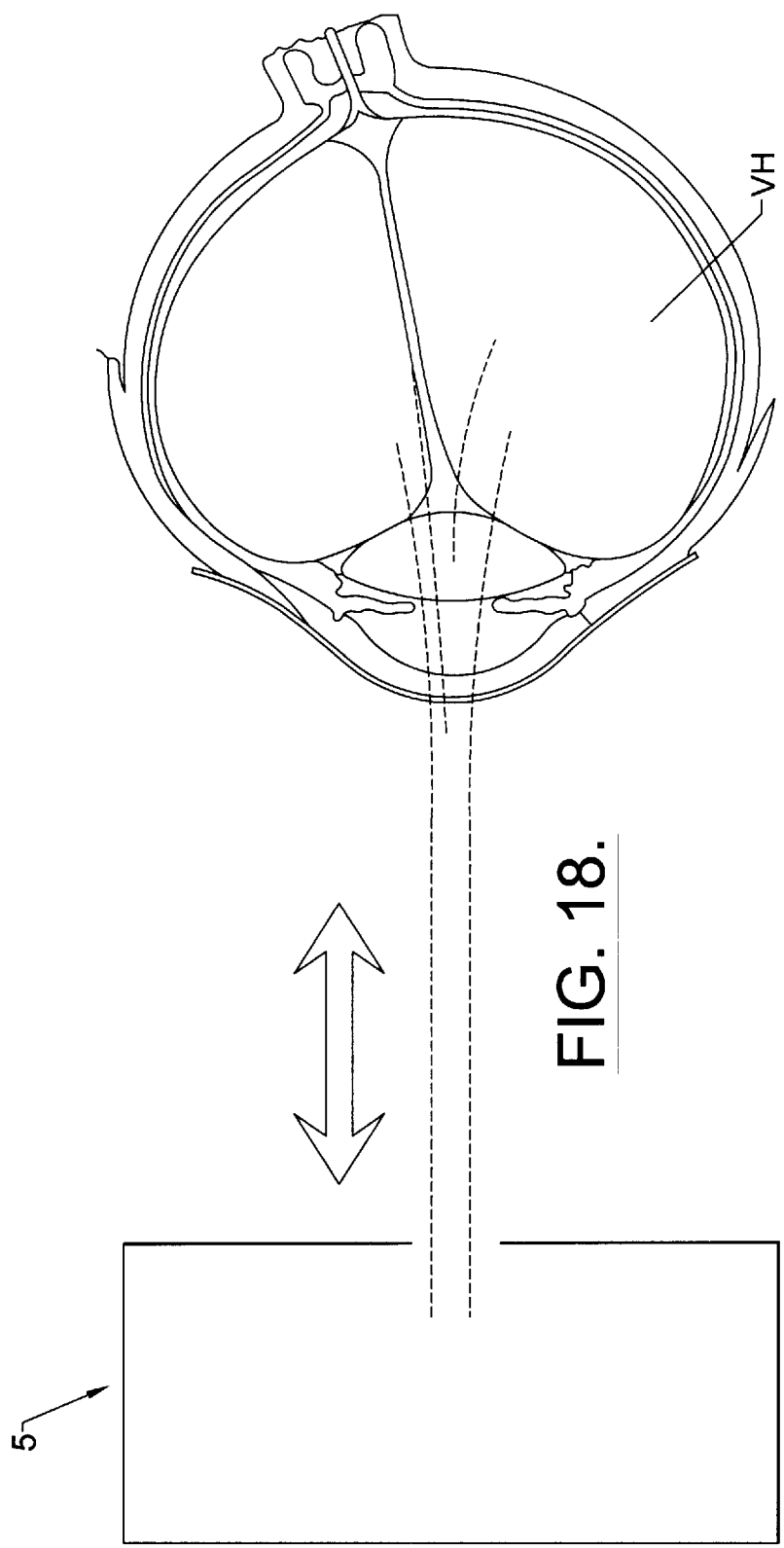
FIG. 18 is a schematic illustration of an apparatus configured to illuminate and obtain the Raman spectrum from the vitreous humor of the eye according to embodiments of the invention.

FIG. 18 illustrates that the illumination target in the eye can be the vitreous humor, a substantially clear gel-like region positioned beyond the aqueous humor. The devices described herein can be configured to operate similarly to that for the AH target, i.e., by transmitting the excitation beam to a deeper depth into the eye and into the VH (through the lens and/or the portion of the eye accessible when the eye is open), illuminating same and then detecting the transmitted light returned therefrom. The energy levels are preferably as noted above for the AH. As the Raman signal from VH may exhibit increased fluorescence, signal correction (subtraction, differentiation, etc..) may be used to obtain/detect the desired signal data.

Figure 19:
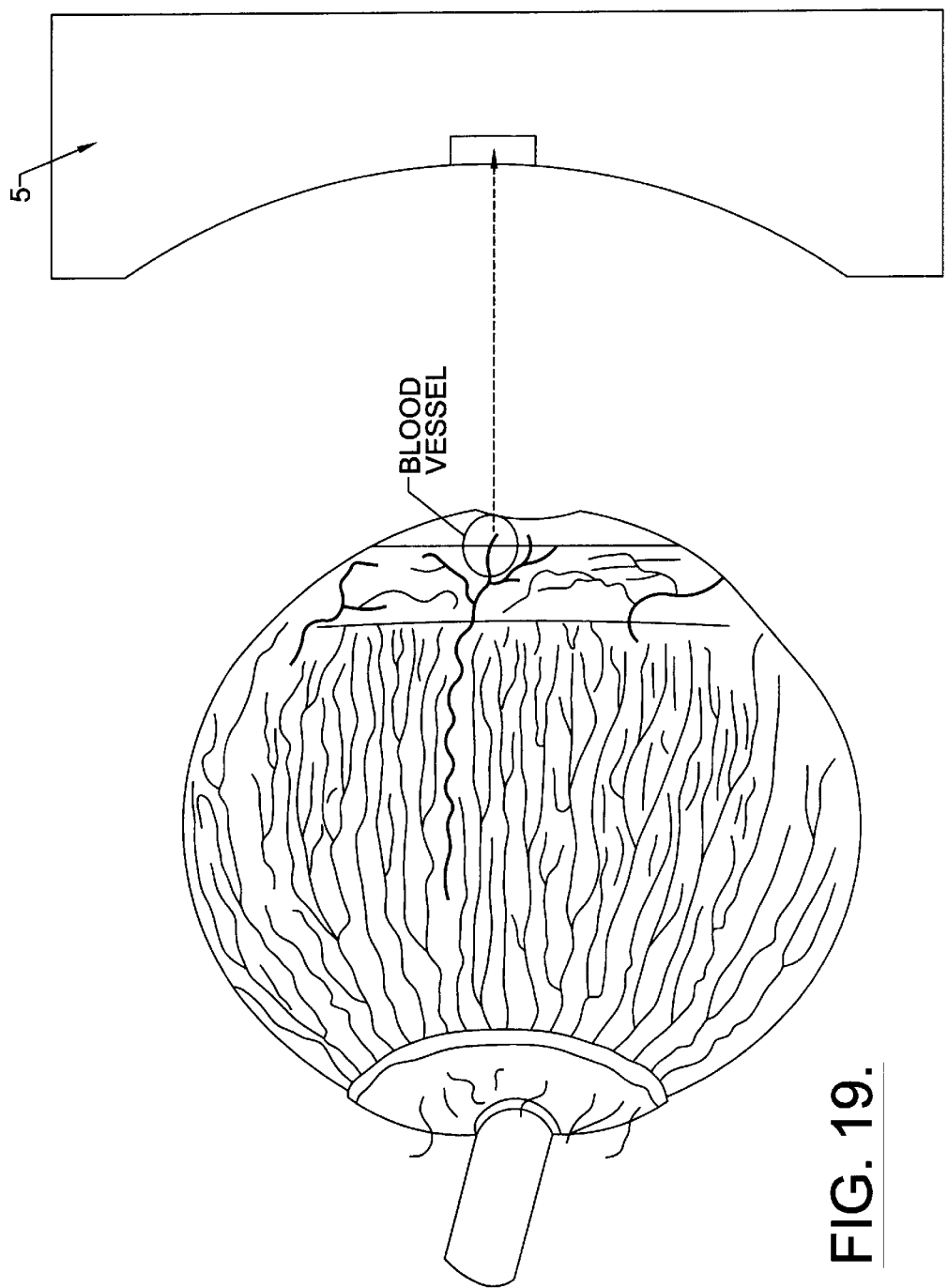
FIG. 19 is a schematic illustration of an apparatus configured to illuminate and obtain the Raman spectrum of one or more blood vessels in the conjunctiva of the eye according to embodiments of the invention.

FIG. 19 illustrates that the illumination target in the eye can be one or more blood vessels located on the conjunctiva at the outer surface of the eye. Using the conjunctiva vessel(s) can allow a direct blood level measurement to be obtained as this embodiment can focus to the blood flowing in the vessel (i.e., the blood itself to directly determine the targeted blood level measurement). In operation, the excitation beam is focused to at least one blood vessel on the externally accessible surface of the eye to illuminate the blood flowing in the blood vessel (because the blood vessel is located on the outer surface of the eye, there is no need to illuminate through skin). The targeted blood vessel can be any of the blood vessels located on or adjacent the conjunctiva of the eye (typically these are visually apparent), such as the long ciliary arteries or veins. One suitable target location may be one of the blood vessels located outside the iris away form the pupil. The detected Raman spectrum signal can be analyzed and a direct blood level measurement of the analyte of interest obtained. In certain embodiments, at least two readings can be taken to obtain data samples at different points of time to watch the spectra change. For example, one can attempt to include data associated with the vessel at a point in time when the blood cells are absent in the illuminated region in the vessel. Further, the Raman signal can be processed (discarded or filtered) to remove the data corresponding to red blood cells to enhance the desired signal of the analyte of interest (such as glucose). In some embodiments, the beam can be altered to disregard the Raman signal of the blood portion and to pursue the Raman signal of plasma (such as by shuttering the beam to discard the blood portion or to delay upon detection of signal associated with blood).

In certain embodiments, the fluorescence spectrum for the aqueous humor can be subtracted from the Raman spectrum by stimulating the aqueous humor with a second excitation laser light pulse at a wavelength slightly different from that of the first pulse (e.g., up to two nanometers from the first pulse), and then subtracting one spectrum from the other in a processor in accordance with conventional techniques. Such techniques are known. See, e.g., Funfschilling and Williams, *Applied Spectroscopy* 30, 443 (1976); Baraga et al., *Applied Spectroscopy* 46, 187 (1992); Wicksted et al., *Applied Spectroscopy* 49, 987 (1995)). In the alternative, the fluorescence spectrum can be subtracted out through the use of software or other processing techniques. Thus, the term "subtraction" as used herein is intended to include techniques such as filtering as well as taking the derivatives of the signal. While not essential, other potentially interfering spectra or signals such as Raman scattering from the lens, iris, or cornea can also be filtered or subtracted through a hardware and/or software processor. Water is typically not an issue for Raman spectroscopy, but a water spectrum can be subtracted if desired.

For the difference spectrum adjustment embodiments, the blood level of the selected substance (or the cerebral spinal fluid level) for the subject can be determined from the difference spectrum by correlating the difference spectrum to predetermined spectrums or data representing the concentration of a particular substance.

The computational analysis can use the differential spectrum or the non-differential spectrum depending on the desired application (typically associated with the degree of fluorescence of the selected region of the eye to determine the Raman spectrum and identify the presence of any selected spectroscopic profile or "signatures" having peaks in a spatial region of the spectrum, which, in turn, allows for the identification of the presence or concentration of a selected substance in the selected region of the eye. The correlation can be based on an empirically based model, formula, or matrix of test data garnered from an actual subject or from in vitro samples. The data can be correlated and the end results computed in a hardware and/or software processor. The model can be obtained through linear (e.g., partial least squares) or nonlinear (e.g., artificial neural networks) multivariate analysis.

In some embodiments, it can be important that a reference set or reference standards of known substances and concentrations be predetermined and stored for computational reference. For example, a training set of Raman spectra can be used. The training set can include samples from (or representative of) the selected region of the eye such as the aqueous humor with a broad range of concentrations of the Raman scattering metabolites. In the training set, the principal Rarnan-scattering metabolites (or "Raman active compounds") should be provided such that they (for at least the AH this may include glucose, lactate, urea, ascorbate, and any exogeneous compounds or drugs present) preferably do not vary co-linearly with one another among the samples in the training set. For direct blood measurements (i.e., the conjunctiva vessel measurements), the Raman active compounds will be those typically present in the blood. The model can be produced with spectra samples obtained from one or more prior subjects, with spectra samples obtained from the subject from whom the current blood level of the analyte of interest is being determined (in which case that subject would be required to provide a blood sample for determination of the blood concentration of the analyte of interest), or from test vials or artificial AH's with known concentrations of selected metabolites and/or the substance of interest. Thus, for an AH-based measurement, a training set can be used, with vials having a plurality of constituents, those normally present in the eye (including lactate, urea, and ascorbate) and in the substance of interest.

In some embodiments, to provide an atypical training sample, an artificial cover (such as a contact lens) may be intentionally positioned over the aqueous humor being used to generate a sample in a training set. This cover or lens can operate to cause the actual AH to have abnormal levels of lactic acid (a lactic acid build up) as it is inhibited from normal operation.

Typically, the training set uses at least 10, and more preferably 20, 25, 30 or more Raman spectra samples (and samples of the corresponding blood levels of each of the selected analytes of interest) with substantial intersample variability in the levels of the major Raman scattering metabolites (e.g., glucose, ascorbate, lactate, urea, and any drugs, analytes, or exogenous compounds present). The concentration of the analyte of interest (in either the blood or aqueous humor) preferably varies by at least a factor of 2, 5, 10 or 20 or more from the sample with the lowest concentration to the sample with the highest concentration. This may include providing concentrations of constituents less than and greatly above their normal levels such as 0.5 times to 15 times the normal levels (for the AH this can include urea, ascorbate, lactate, and, can also include glucose or other substances of interest, in saline). The mixtures can be prepared such that they provide a statistically uniform distribution with no bias/co-linearity (i.e., 100 different mixtures of four random substances in the test tube). It is anticipated that the calibration curve can be biased to cluster a training set biased within the normal or low range (i.e., to be skewed, depending on the application).

The concentration ratios or correlations may require development of the model using subjects with multiple different diseases (e.g., renal failure, diabetes, seizures, mitochondrial myopathies, sickle cell disease, heart failure, blood clots, etc.) and/or other parameters such as gender, age, weight, national origin, etc. For human applications, the model may even be determined with spectra samples obtained from animals, particularly primates. The sample of the selected region in the eye may be a natural sample (human or animal), or may be a man-made or surrogate aqueous humor sample created to mimic natural samples, where the blood level is calculated from a priori knowledge of the relationship between blood levels and aqueous humor levels for the analyte(s) of interest (for the blood level measurements). Similarly, for the cerebral spinal or intracranial fluid, the aqueous humor sample may be a natural sample (human or animal), or may be a man-made or surrogate aqueous humor sample created to mimic natural samples, where the level is calculated from a priori knowledge of the relationship between cerebral spinal or intracranial levels and aqueous humor levels for the analyte(s) of interest.

For example, when the analyte of interest is glucose, the training set of samples for the empirical model can comprise at least 20, 25 or 30 aqueous humor spectra samples. The samples can include varying levels of constituents which correspond to measured blood glucose levels, where the principal Raman active compounds in the aqueous humor samples (glucose, ascorbate, lactate, urea, and preferably any exogenous compounds such as drugs) vary substantially non-colinearly among the samples. The physiological levels of the blood and/or corresponding aqueous humor glucose concentration in the test samples can range from 0 or 50 mg/dL to 800 or 1,000 mg/dL, typically including at least a 100, 200, 300 or 400 mg/dL difference in concentration between the sample with the lowest concentration and the sample with the highest concentration.

Figure 12:
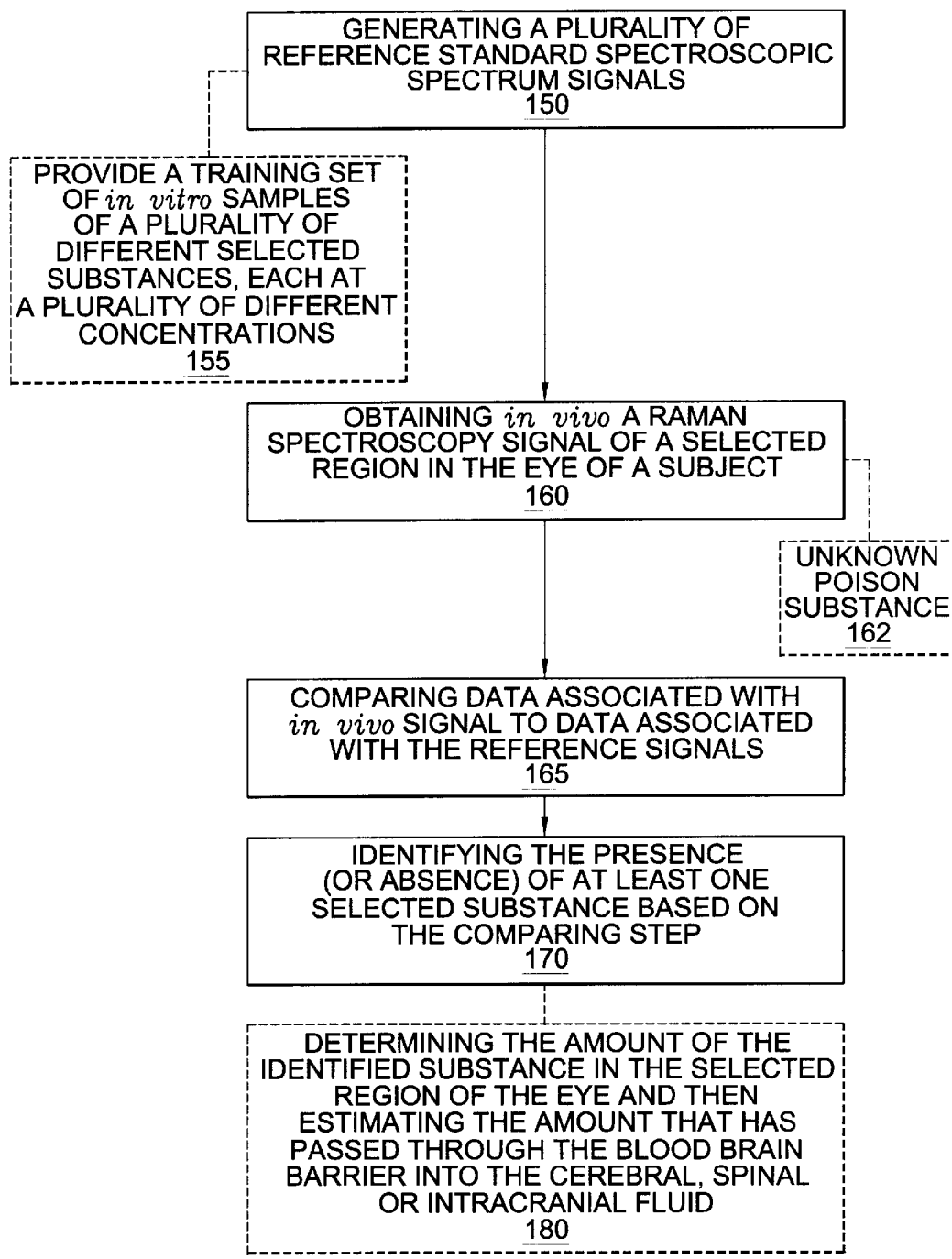
FIG. 12 is a block diagram of a method for identifying the presence of at least one selected substance in a selected region of the eye of a subject to evaluate the quantity of same in the cerebral spinal or intracranial fluid (it being assumed that the mechanics of the blood aqueous barrier can be representative to the blood brain barrier, the same having passed through the blood brain barrier) according to certain embodiments of the present invention.

Turning now to FIG. 12, one embodiment of the invention illustrated therein is particularly suited for the non-invasive detection, identification and/or measurement of poison in the blood. A plurality of reference standard spectroscopic spectrum signals are generated (Block 150). The reference signals can be converted into data defining peaks and frequencies and features of interest and the standards can correspond to in vitro samples of a plurality of different selected substances, and in some embodiments, each presented at different concentration levels (Block 155). The data associated with the reference standards can be programmed into a computer or signal processor and made available for subsequent use. As noted above, the reference standards can correspond to a plurality of different Raman spectrum data corresponding to a plurality of different drugs, or typical or common poisonous substances. For example, Raman signatures of the most prevalent chemicals associated with pediatric poison control calls or emergency room visits can be analyzed in various concentrations to define an associated Raman signature. These can include common over-the-counter household drugs or medicinal supplies such as the drugs identified by brand names acetaminophen, ibuprofen, isopropyl alcohol, methanol, ethylene glycol and the like, or prescription drugs Such as blood pressure medicines (such as HYTRTN), steroids, antibiotics, birth control pills, and the like, as well as household cleaning chemicals, pesticides, herbicides, and petroleum products.

An in situ Raman spectroscopic reading can be obtained of the subject (Block 160). The subject may have been exposed to an unknown poison or substance. In some embodiments, the term "unknown poison or substance" can also include an unknown quantity of a known substance. For example, a guardian acknowledges that a TYLENOL bottle was found empty next to a young child, but it is unknown how many pills may have been in the bottle. The present invention may be able to determine whether a toxic amount was consumed.

In any event, the presence (or absence) of at least one selected substance in the subject can be identified (Block 170). The amount of the identified substance in the selected region of the eye of the subject may also be determined. Based on the amount in the eye, an amount (a) in the blood and/or (b) in the cerebral spinal fluid or intracranial fluid can be established (anticipating that the amount in the AH can be correlated to either the amount in the blood or the amount in the cerebral spinal or intracranial fluid), thus allowing the presence and concentration to be indirectly established or estimated based on the detected presence and/or concentration in the selected region of the eye (such as the AH) (Block 180). Physiological differences among different population segments may require determination of different correlation factors for each population segment (segmented by selected parameters of interest such as by age, gender, national origin, etc.)

In one embodiment, a Raman spectra/spectrum poison control substance identification database can be generated and the in situ reading then compared thereto so that a screening and assessment of the identity of which poison or poisons that the subject has been exposed can be readily identified by matching the in situ reading to one or more of the pre-determined and digitally stored Raman spectra. The database of selected substances may be held on a central database which can be remotely located or located at regional or selected locations (via the internet, intranet, or other communication means) and the localized reading can be uplinked to the larger database for a more comprehensive screening. Alternatively, the signal processor or computer associated with the Raman excitation/detection device or system may be configured with data corresponding to the most common types of substances and if a localized scan fails to match the in situ reading, a more comprehensive computational screening can be performed off-line or at the remote or larger database location.

Figure 13:
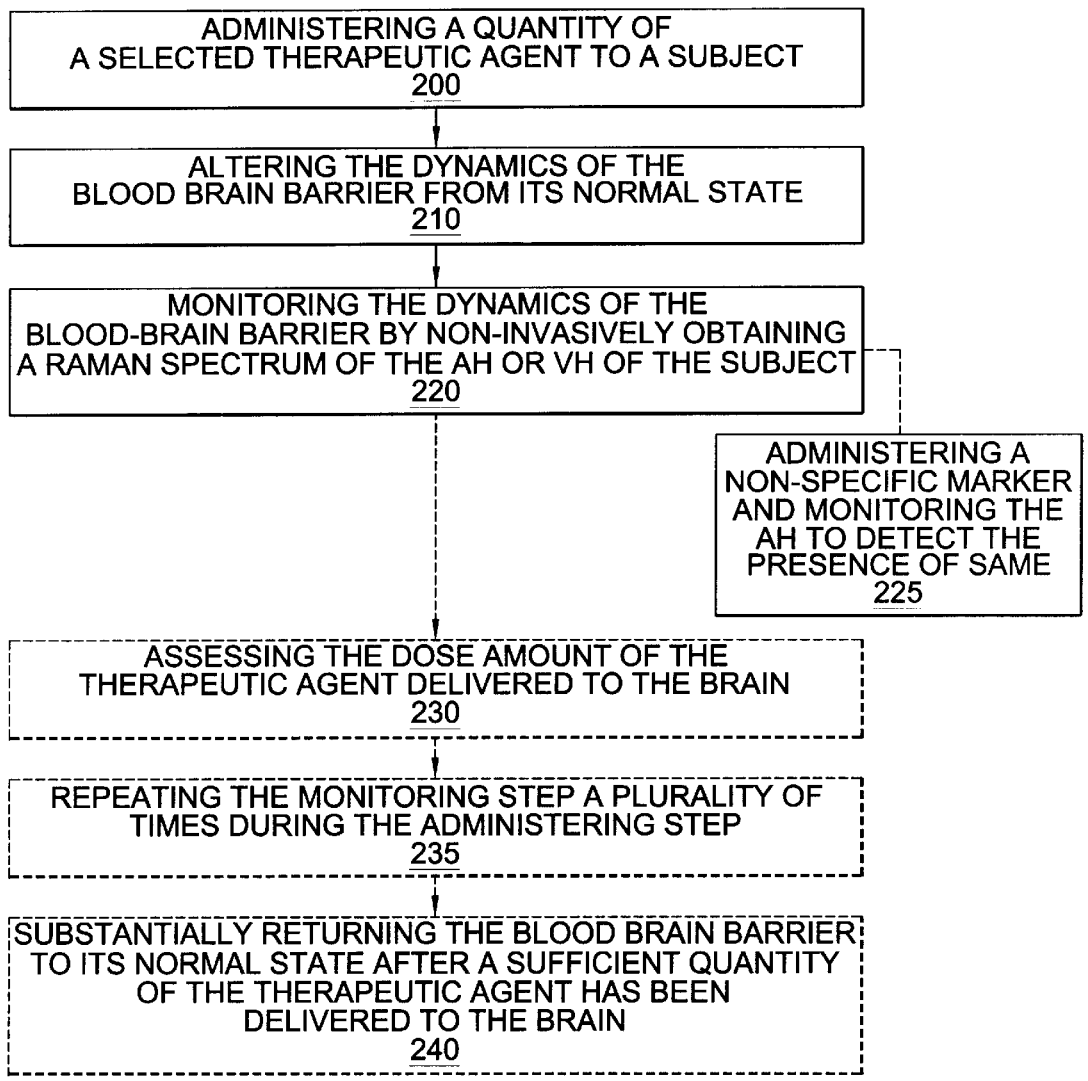
FIG. 13 is a block diagram of a method for monitoring or treating a patient by administering a therapeutic agent during a chemotherapy session patient according to embodiments of the present invention.

As shown in FIG. 13, another embodiment of the present invention is directed to an in vivo method for monitoring the administration of a targeted therapy such as a drug, chemical, gene, or other therapy, given to a subject for treatment of a condition in the brain (such as various cancers or neurologic conditions). For example, the present invention may be used during a treatment session using delivery of a cytotoxic agent to treat a cancerous tumor in the brain (or to other patients for specialized drug treatments targeted to the brain such as for treating neurological impairments in the brain). The method includes administering a dose of a selected treatment agent (typically chemotherapy) to a subject (Block 200). The dynamics of the blood brain barrier are deliberately or intentionally altered from the normal state (Block 210). The dynamics or function/operation of the blood brain barrier are monitored by non-invasively obtaining the Raman spectrum of the aqueous humor (Block 220). A physiologically suitable non-specific marker, selected for its normal reluctance to cross the blood brain barrier, can be administered to the subject (Block 225), and the monitoring step can be carried out by identifying its presence in the selected region of the eye (typically in the AH, but the vitreous humor or "VH" may also be suitable in certain embodiments). The non-specific marker can be synthetic or natural as noted (such as an antibiotic or conjugated billirubin or other suitable analyte).

The dose of the (chemotherapeutic) agent delivered to the brain can be estimated by determining the concentration in the AH (Block 230). The monitoring step can optionally be repeated a plurality of times during the administering step (Block 235). The blood brain barrier can be returned substantially to its normal state after a sufficient quantity of (chemotherapeutic) agent has been delivered to the brain (Block 240). The altering step can be carried out by administering a chemical which can be flushed from the system or the dosing terminated to allow the normal function to return. In some embodiments, the non-specific marker can be the therapeutic agent itself.

In one embodiment, the altering step is carried out by introducing an osmotic agent or chemical (such as a drug identified by a trade name of MANATOL) to the subject to temporarily open the blood brain barrier to allow larger molecules to pass therethrough. In another embodiment, the altering step can be carried out by increasing the intracranial pressure of the subject (such as by positioning the subject in a pressurized chamber).

Figure 14:
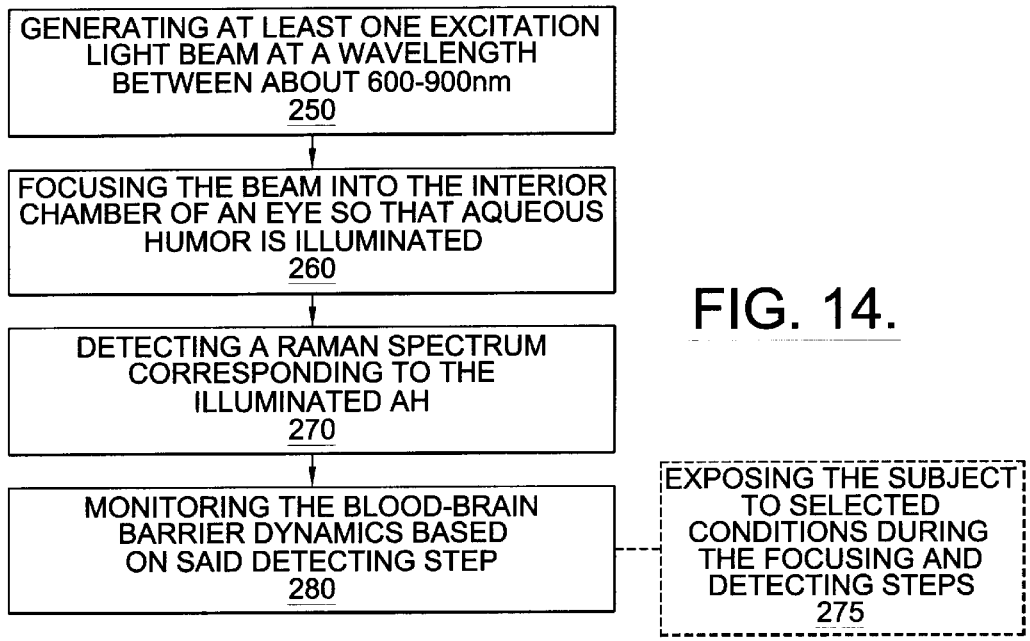
FIG. 14 is a block diagram of a method of monitoring the blood brain barrier dynamics of a subject during exposure to selected conditions according to embodiments of the present invention.

Another embodiment is shown in FIG. 14. This embodiment is directed to a method of non-invasively monitoring the operation/function of the blood brain barrier (which can include detecting any change from a normal state). The method comprises the steps of: (a) generating an excitation beam at a wavelength of from 600 to 900 nanometers (Block 250); (b) focusing the excitation beam of said generating step into the anterior chamber of an eye of the subject so that aqueous humor in the anterior chamber is illuminated (Block 260); (c) detecting a Raman spectrum corresponding to the illuminated aqueous humor (Block 270); and (d) monitoring the blood brain barrier dynamics based on the detecting step (Block 280). The method may also include the step of exposing the subject to selected conditions during the focusing and detecting steps (Block 275).

In certain embodiments, the monitoring step can be used to assess whether the dynamics thereof alter sufficiently to allow selected analytes, which would normally be inhibited from traveling through the blood brain barrier, to pass into the intracranial spinal fluid through the blood brain barrier. This can be useful for clinical trials or assessments of new drugs or treatment therapies. In other embodiments, the monitoring step can be carried out when a person is under or exposed to extreme conditions such as when diving, flying, or mountain climbing, or when suffering from a traumatic head or brain injury, high stress, or the like.

The method can also include the steps of comparing the Raman spectrum from the detecting step to reference spectrums corresponding to at least one selected analyte of interest, and indirectly identifying the presence of the least one analyte of interest in the subject's cerebral spinal fluid based on the detecting and comparing steps.

FIG. 15 illustrates yet another embodiment of the present invention. This method for identifying an alteration in the blood brain barrier of a biological subject comprises the steps of: (a) non-invasively obtaining a first in vivo Raman spectrum of the aqueous humor of the subject (Block 300); (b) non-invasively obtaining a second in vivo Raman spectrum of the aqueous humor of the subject (Block 310); (c) comparing the first and second readings (Block 320); and (d) detecting an alteration in the blood brain barrier by comparing the first and second Raman spectrums (Block 330).

Figure 16:
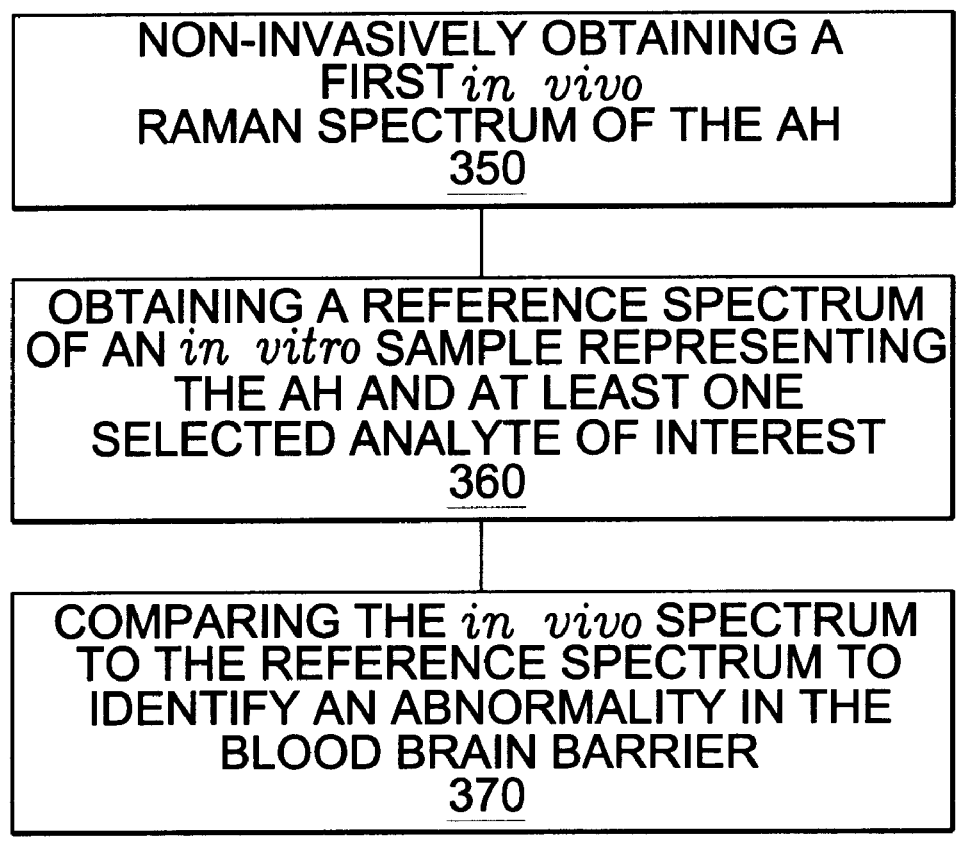
FIG. 16 is a block diagram of a method for identifying an abnormality in the blood brain barrier of a subject according to embodiments of the present invention.

In another embodiment, shown in FIG. 16, a method for identifying an alteration in the blood brain barrier of a biological subject comprises the steps of: (a) non-invasively obtaining a first in vivo Raman spectrum of the AH of the subject (Block 350); (b) obtaining a reference spectrum of an in vitro sample representing the aqueous humor and comprising at least one selected analyte (Block 360); and (c) comparing the in vivo Raman spectrum to the reference spectrum to identify an abnormality in the blood brain barrier (Block 370). The abnormality may be indicated by detecting in the AH the presence of at least one selected analyte (typically one which is normally inhibited from passing through the blood brain barrier because of its molecular size or permeability and, as such, is not normally present in the intracranial fluid) thereby its presence in the AH also indicates its presence in the intracranial fluid of the subject.

The at least one selected analyte can be one which typically does not cross the blood brain barrier so that a determination of its presence in the sample is indicative of an abnormality or impairment or successful intentional alteration of the blood brain barrier dynamics. In one embodiment, the at least one selected analyte can be a bacteria.

Figure 17:
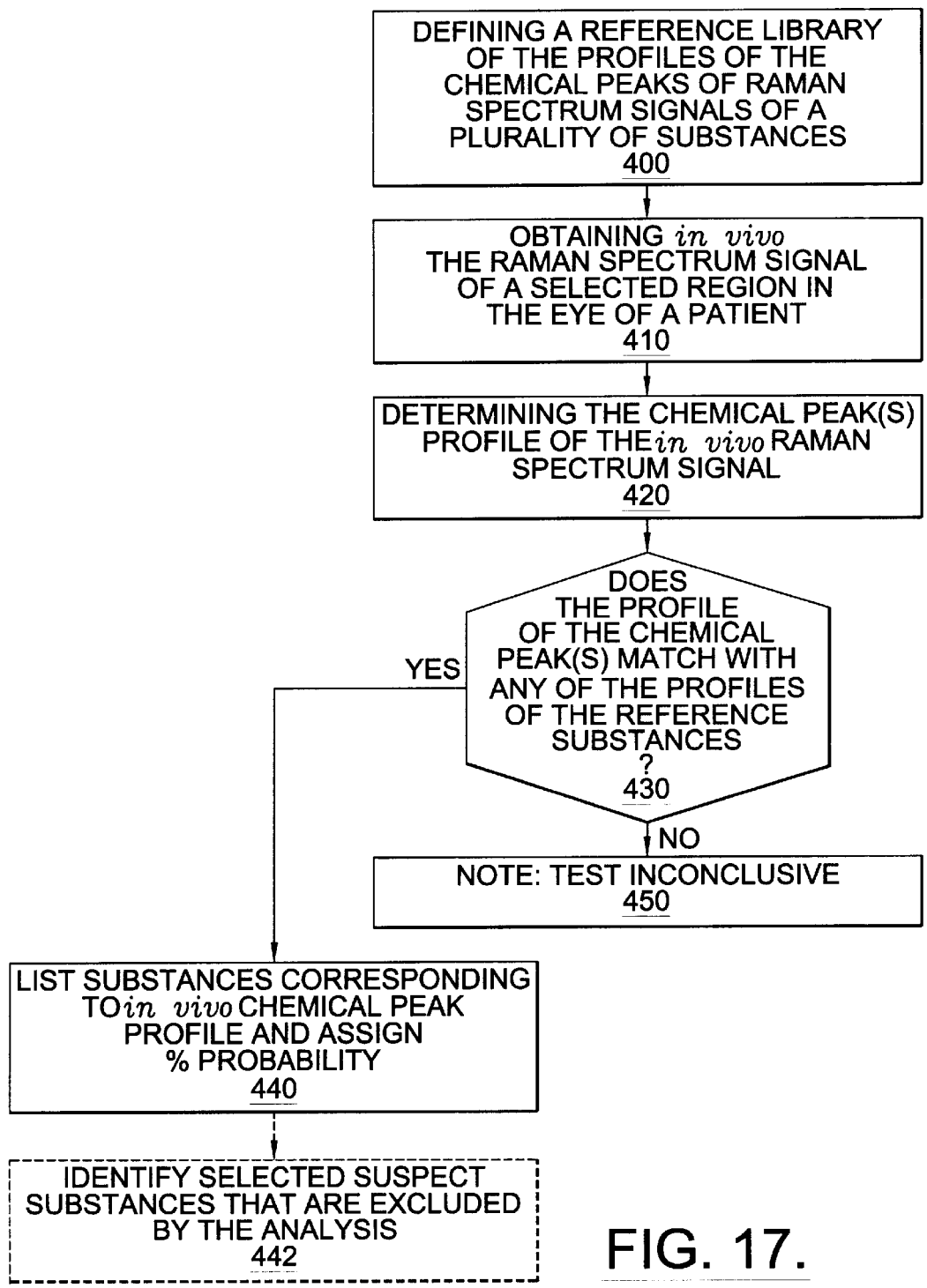
FIG. 17 is a flow chart of a method according to one embodiment of the present invention.

FIG. 17 illustrates an additional embodiment of the present invention. In this embodiment, a reference library of the profiles of the chemical peaks (chemical peak profiles can also include the chemical valleys or line shapes) of the Raman spectra signals of a plurality of substances can be established or generated (Block 400). This can include providing the chemical peak profiles for each of the plurality of the substances at different concentrations. A Raman spectrum signal can be obtained in vivo of the AH (or VH)

of the eye of a subject (Block 410). The chemical peak profile of the in vivo obtained Raman signal can be determined (Block 420). Next, the profile of the in vivo data is compared to the reference library to see if there is a statistical correlation (or best fit match) between one or more of the library profiles with the in vivo obtained profile (Block 430). If the answer is yes, then a list of one or more substances can be generated with a percent correlation of the likelihood of the match (Block 440). The method may also rule out potential suspects (Block 441). The list is likely to include one or more substances, as many will contain chemicals with overlapping peaks, but the presence or absence of other peaks can help statistically fit the data to identify the closest matches. If there is no match, or the correlation percentage is below a certain threshold (such as below 20–50%), then the test can be identified as inconclusive (Block 450). The method may also allow a physician to query whether as suspect drug or substance is indicated, which may for example, consider whether a particular "suspect" substance which is believed to be the ingested or consumed poison may be in the subject. In turn, the method can respond to the inquiry to exclude the substance as a suspect with an identified statistical percentage (i.e., 95% confidence level that substance is not methanol) or to otherwise note the probability of this as the poison (i.e., 5% probability that the substance is methanol).

As will be appreciated by one of skill in the art, the present invention may be embodied as a device, method, or system comprising a digital processing system, and/or computer program product. Accordingly, the present invention may take the form of an entirely hardware embodiment or an embodiment combining software and hardware aspects. Furthermore, the present invention may include a computer program product on a computer-usable storage medium having computer-usable program code means embodied in the medium. Any suitable computer readable medium may be utilized including hard disks, CD-ROMs, optical storage devices, or magnetic storage devices.

The computer-usable or computer-readable medium may be or include, for example, but not limited to, an electronic, magnetic, optical, electromagnetic, infrared, or semiconductor system, apparatus, device, or propagation medium. More 10 specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM), a CD ROM, a DVD (digital video disk), or other electronic storage medium. Note that the computer-usable or computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

Computer program code for carrying out operations of the present invention may be written in an object oriented programming language such as Java®, Smalltalk or C++. However, the computer program code for carrying out operations of the present invention may also be written in conventional procedural programming languages, such as the "C" or FORTRAN programming language or even assembly language. The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The present invention is described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, embedded processor or other programmable data processing apparatus to produce a machine, such that the instructions, which execute via the processor of the computer or other programmable data processing apparatus, create means for implementing the functions specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture or output a test result including instruction means which implement the function specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

As is seen in FIGS. 10*a, b, c,* FIGS. 5 and 6, the system 5 includes a signal processor or controller 32*s*. The signal processor or controller can be a general purpose microprocessor, a digital signal processor or a specific purpose processor. The signal processor can be an electronic device, a software or program-implemented device running on a general-purpose computer, or combinations of such. The present invention should not be construed as limited to the particular configurations illustrated in the figures but is intended to encompass other configurations capable of carrying out the operations and/or functions described herein.

The signal processor 32*s* can be any commercially available or custom microprocessor. The computer 32 or signal processor or controller may include a data processing system with I/O data port(s) or other such devices that also communicate with the processor. The I/O data port can be used to transfer information between the data processing system or signal processor 32*s* and another computer system or a network (e.g., the Internet) or to other devices controlled by the processor. These components may be conventional components such as those used in many conventional data processing systems which may be configured in accordance with the present invention to operate as described herein.

The devices or the present invention may include memory devices containing the software and data used to implement the functionality of the data processing system or signal processor 32*s*. The memory can include both programmable and read-only memory. Typical programmable memory includes, but is not limited to static RAM (SRAM), dynamic RAM (DRAM), flash RAM, EEPROM or other such programmable memory devices whose contents may be modified. The read only memory may be of a type which may not be modified after its initial programming, such as ROM or PROM but may also be programmable in certain embodiments of the present invention.

The memory may contain several categories of software and data used in the data processing system or system processor: the operating system; the input/output (I/O) device drivers; and the image (and/or in the case of dual stimulus, the auditory) data. As will be appreciated by those of skill in the art, the operating system may be any operating system suitable for use with a data processing system, such as OS/2, AIX or OS/390 from International Business Machines Corporation, Annonk, N.Y., WindowsCE, WindowsNT, Windows95, Windows98 or Windows2000 from Microsoft Corporation, Redmond, Wash., PalmOS from Palm, Inc., MacOS from Apple Computer, UNIX or Linux, proprietary operating systems or dedicated operating systems, for example, for embedded data processing systems.

The I/O device drivers typically include software routines accessed through the operating system to communicate with devices such as the input devices, the display 25 (FIG. 7), the I/O data port(s), and certain components of the memory. The data can be static and dynamic data used by the operating system, I/O device drivers, the detector, and other software programs that may reside in the memory.

While the present invention is described, for example, with reference to particular divisions of programs, functions and memories, the present invention should not be construed as limited to such logical divisions. Thus, the present invention should not be construed as limited thereto as it is intended to encompass any configuration capable of carrying out the operations described herein.

The present invention is explained in greater detail in the following non-limiting Examples, in which "$\mu L$" means microliters; "dL" means deciliters, "mW" means milliwatts, "nm" means nanometers, "Kg" means kilograms, "J" means Joules, "$cm^2$" means square centimeters, and temperatures are given in degrees Centigrade.

EXAMPLE 1

Measurement of Aqueous Humor Glucose In Vitro with Raman Spectroscopy

Aqueous humor was obtained from sixteen New Zealand white rabbits within one minute of sacrifice by other investigators. These animals had experienced experimental myocardial infarction 48 hours prior to euthanasia. They were sacrificed by rapid exsanguination under ketamine and xylazine anesthesia. Aqueous humor samples were kept frozen until glucose levels could be measured and Raman spectroscopy performed. Glucose concentration was measured with a commercial glucometer (Glucometer Elite, Bayer, Elkhart, Ind., USA) and confirmed against concentration standards. Each measurement was repeated, and the average measurement was considered actual glucose concentration.

Samples were placed in conical quartz cuvettes designed to hold a volume of 80 $\mu L$ and permit direct optical access to the solution by the spectrometer without traversing glass walls or coverslips.

Raman spectroscopy was performed with a f/1.8 holographic imaging spectrograph (Kaiser Optical Systems, Ann Arbor, Mich., USA) attached to an Olympus Bx60 microscope with 10x objective. Data were collected using a Princeton Instruments (Trenton, N.J., USA) camera with a 1024×256 CCD array (EEV, United Kingdom) cooled to −80° C. with liquid nitrogen. Illumination of the sample through the microscope objective was achieved with a Ti:Sapphire laser (Spectra Physics 3900S, Mountain View, Calif., USA) pumped by an argon laser (Spectra Physics 2010E). Spectrographic data was integrated while the sample was illuminated at a wavelength of 785.0 nm (30 mW) for 10 seconds. This illumination was then repeated at a wavelength of 787.2 nm.

The integrated spectra at the two slightly different wavelengths were then subtracted from one another. This effectively eliminates the broadband fluorescence, which does not shift relative to the excitation wavelength. It leaves the Raman-shifted spectra appearing as a bipolar pattern (FIG. 1).

Multivariate analysis of the spectra was accomplished using Holograms (Princeton Instruments, Trenton, N.J.) and Grams (Galactic Industries, Salem, N.H. USA) software packages. Thirty-two aqueous humor samples (from sixteen rabbits) were evaluated using a "round robin" approach to iteratively group all but one of the samples into a training set. Hence, the system trains on all but one of the samples, estimates the glucose level in that sample, then rotates the test sample into the training set. This cycle is repeated until all samples have served as an unknown test sample.

A back propagation neural network (D. Rumelhart et al., Nature 323, 533 (1986))was employed to determine if a nonlinear regression method would better predict the glucose concentration from the Raman spectra of aqueous humor. Such a model may compensate for as yet unknown interactions between analytes in aqueous humor. A two-layer back propagation neural network (NeuralWare, Inc., Pittsburgh, Penn., USA) was employed using a sigmoidal function as the nonlinear element. Factors derived from the partial least squares algorithm served as the inputs to the neural network. Raw spectral data could have been used but would have required a prohibitively large training set. As in the linear regression preformed earlier, round robin training and testing was utilized. During training, the neural network's weights were adjusted to minimize the total squared error between the actual glucose concentration and the predicted glucose concentrations. Each sample was tested using a neural network trained on the remaining 31 samples.

EXAMPLE 2

Correlation of Aqueous Humor Glucose with Rising Blood Glucose

Nine female New Zealand white rabbits were used for this part of the study. They were anesthetized with ketamine (50 mg/kg) and xylazine (7.5 mg/kg) given as a single intramuscular injection. Xylazine blocks release of insulin from the pancreas and causes blood glucose to rise (K. Chalabi et al., Ophthalmic Res. 19, 289 (1987); J. Arnbjerg et al., Ophthalmic Res. 22, 265 (1990)).

Blood samples were taken from the central ear arteries at various times following the injection of anesthetic once the animals were adequately anesthetized. Whole blood was immediately measured for glucose concentration with a commercial glucometer (Glucometer Elite, Bayer). In most instances two measurements were made. The average measurements are reported. If the measurements differed by more than 20%, a third measurement was made. If one measurement differed by more than 20% from the mean, it was discarded. In instances when blood glucose concentration appeared stable, occasionally only one measurement was made.

At various times after induction of anesthesia, samples of aqueous humor were taken. This was done by paracentesis with a 25-gauge needle through clear cornea near the limbus after administration of proparacaine eye drops. Aqueous humor glucose concentration was measured with the glucometer in a manner similar to the blood.

In rabbits, there is massive breakdown of the blood-aqueous barrier after a single paracentesis of the anterior chamber of the eye (W. Unger et al., *Exp. Eye Res.* 20, 255 (1975)). The aqueous humor becomes too viscous for repeat paracentesis for at least 30 minutes. Consequently, the results are reported for the first paracentesis of an eye. In a few instances, however, a second paracentesis was made an hour later to assess how the breakdown of the blood-aqueous barrier may have affected the correlation of aqueous glucose with plasma glucose.

Average blood glucose concentrations for each animal were plotted against time after anesthetic injection. Since it was not possible to obtain blood samples simultaneous with aqueous humor samples, a best-fit second-order polynomial was calculated for each animal. This was used to calculate the blood glucose concentration at the time that the aqueous humor sample was taken. Aqueous humor glucose concentration was then plotted against the calculated simultaneous blood glucose concentration for all animals. DeltaGraph software (Delta Point, Inc., Monterey, Calif. USA) was used for all statistical calculations.

EXAMPLE 3

Results for Measurement of Aqueous Humor Glucose In Vitro with Raman Spectroscopy The raw spectra of rabbit aqueous humor show broad fluorescence peaks that obscure the underlying Raman signature (FIG. 1). When the spectra from the two slightly different wavelengths are subtracted, one from the other, the Raman shifted spectra become apparent as bipolar peaks.

Figure 2:
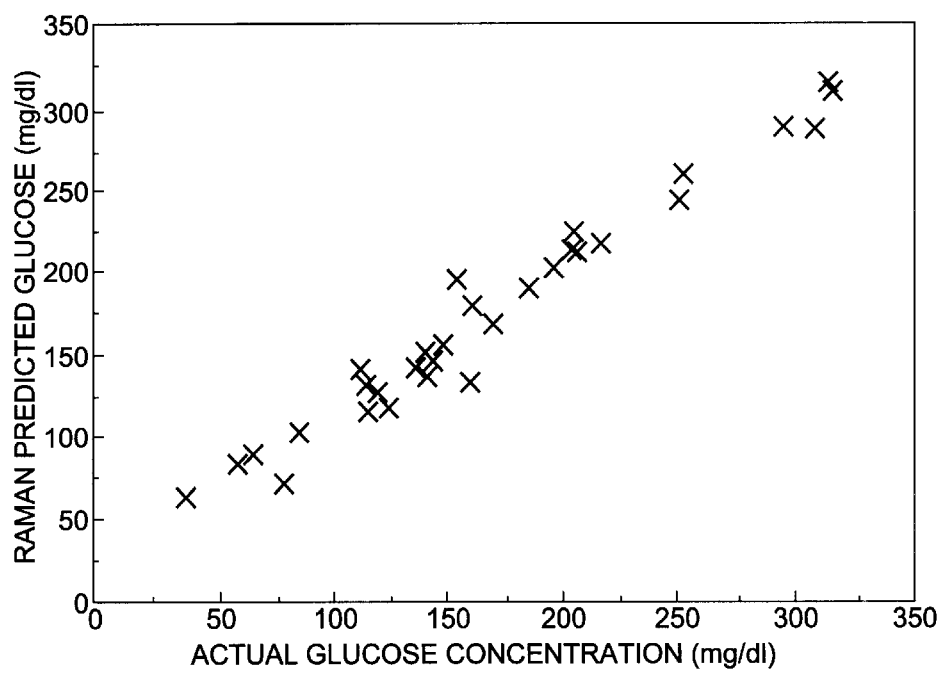
FIG. 2 is a graph plotting Raman predicted glucose as a function of actual glucose concentration. The glucose concentration in aqueous humor from 16 rabbits was estimated with Raman spectroscopy and compared to the actual glucose concentration measured with a commercial glucometer. The graph shows the Raman predicted glucose concentration after subtracting fluorescence and applying a linear partial least square algorithm followed by nonlinear back propagation with an artificial neural network. This resulted in a high degree of correlation ($r^2=0.98$) of predicted with actual glucose concentration. Applying the partial least squares algorithm alone resulted in lesser correlation ($r^2=0.90$).

Actual aqueous humor glucose concentration, measured by the glucometer, ranged from 37 to 323 mg/dL in the thirty-two samples. Multivariate analysis of the raw spectra from these samples with the partial least squares algorithm revealed fair correlation ($r^2=0.76$) between the predicted aqueous humor glucose concentration and the actual concentration. Multivariate analysis of the subtracted spectra from these samples with the partial least squares algorithm resulted in improved correlation ($r^2=0.90$) between the predicted aqueous humor glucose concentration and the actual concentration. When back propagation with an artificial neural network is further applied to the data, correlation is excellent ($r^2=0.98$) (FIG. 2).

EXAMPLE 4

Results for Correlation of Aqueous Humor Glucose with Rising Blood Glucose

Figure 3:
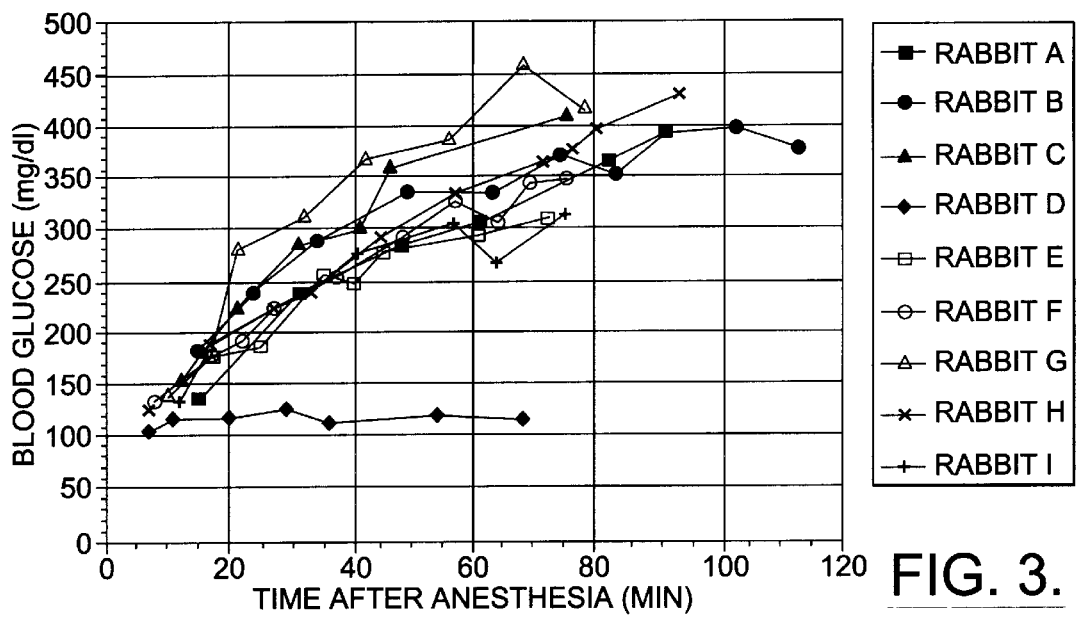
FIG. 3 is a graph plotting blood glucose as a function of time. Blood glucose steadily rises at variable rates in rabbits after administration of xylazine anesthesia. One animal (rabbit D, filled diamonds) had little change in blood glucose for unknown reasons.

The rate of rise of blood glucose after xylazine injection is highly variable from animal to animal (FIG. 3). In fact, in one rabbit there was little change in the blood glucose concentration over time.

Figure 4:
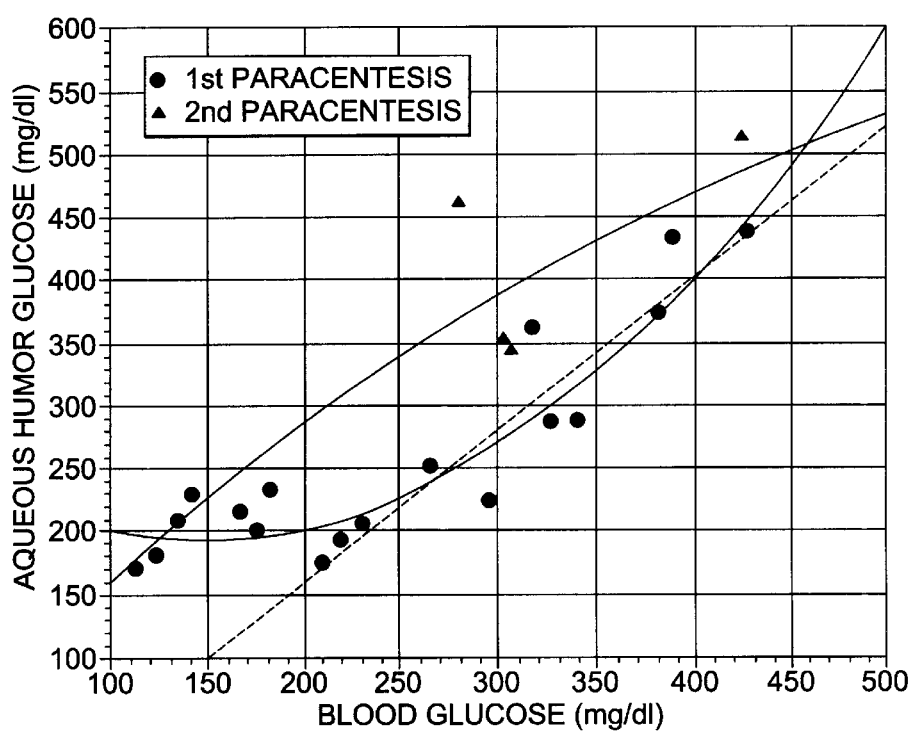
FIG. 4 is a graph plotting aqueous humor glucose as a function of blood glucose. Best-fit second-order polynomial curves demonstrate the relationship between aqueous humor glucose and plasma glucose while plasma glucose is rising in 9 animals. Aqueous glucose measurements from the first paracentesis of an eye correlate well with simultaneous plasma glucose (dark curve). When plasma glucose exceeds 200 mg/dL the relationship is nearly linear (dashed line). Aqueous humor glucose exceeds plasma glucose when plasma glucose is less than 200 mg/dL. The relationship of aqueous humor glucose with plasma glucose is different when the aqueous humor sample is obtained as a second paracentesis (light curve) suggesting that the initial paracentesis disrupts normal glucose homeostasis.

If only samples taken in the first fifteen minutes after anesthetic injection are considered, aqueous humor glucose concentration is higher than blood glucose concentration (207±28 mg/dL for aqueous humor; 135±27 mg/dL for blood). When calculated blood glucose rises above 200 mg/dL, simultaneous aqueous humor glucose parallels blood glucose nearly linearly [aqueous humor glucose=1.18 (blood glucose)−72.7; $r^2=0.88$] (FIG. 4).

The number of aqueous humor samples from second paracenteses was insufficient to draw conclusions about their significance. They did not appear, however, to correlate well with aqueous humor glucose levels from initial paracenteses (FIG. 4).

These data indicate that the baseline ratio of aqueous humor glucose to blood glucose in rabbits is approximately 1.5. (It may actually be higher than this as a true baseline was not obtained, and the blood glucose levels were likely elevated by the time the first samples were obtained, even in the first 15 minutes after injection.) This is much higher than in humans and higher than in previous reports on rabbits. All previous reports on rabbits, however, were prior to recognition of the hyperglycemic effect of xylazine anesthesia, yet many of them used xylazine anesthesia. In addition, most previous reports assumed that the rabbits were at steady-state euglycemia, without actually confirming that this was the case. These facts may account for some of the highly variable results in previous reports.

These data also demonstrate that aqueous humor glucose in the rabbit responds almost immediately once blood glucose exceeds 200 mg/dL. The relationship of aqueous humor glucose to blood glucose is nearly linear while blood glucose is rising above 200 mg/dL. Below that level, aqueous humor glucose appears stable. What happens to aqueous humor glucose when blood glucose is clamped at a hyperglycemic level, or when blood glucose concentration drops, has yet to be determined. Nonetheless, equilibration of aqueous humor glucose with blood glucose probably occurs within minutes in rabbits. If rapid equilibration of aqueous humor glucose also occurs in humans, it could serve as an excellent substrate for non-invasive glucose monitoring.

Previous investigators have found no breakdown in the blood-aqueous barrier of albino rabbits exposed to infrared radiation with energy densities up to 106 J/cm (D. Reddy, supra; G. Peyman et al., *Exp. Eye Res.* 42, 249 (1986); T. Kumik et al., *Inv. Ophthalmol. Vis. Sci.* 30, 717 (1989)). Infrared energy densities as low as 44 J/cm² may be sufficient to breakdown the blood-aqueous barrier in pigmented rabbits, however. This is still substantially higher than the energy density that would need be applied with the Raman technique disclosed herein.

Figure 21A:
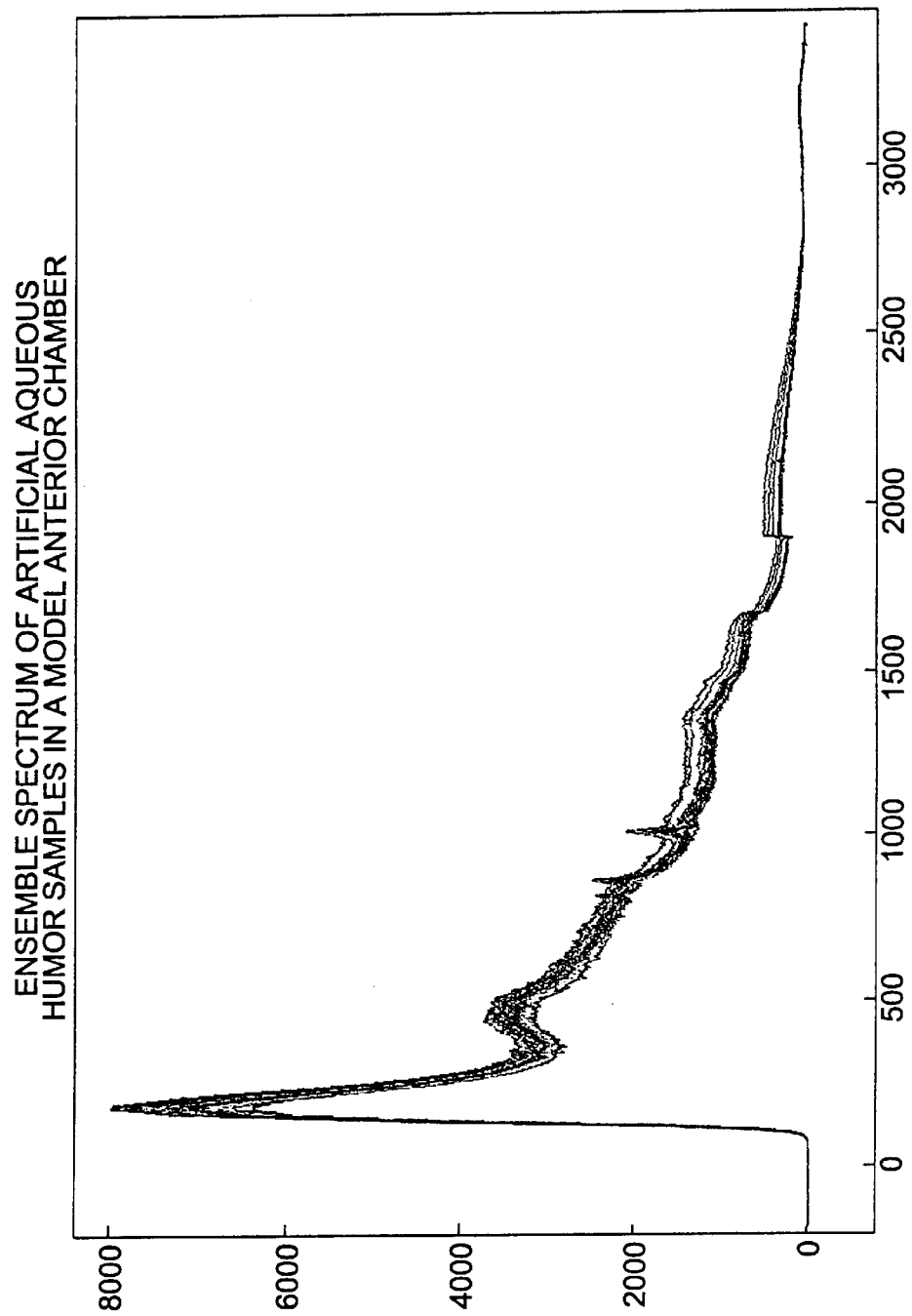
FIGS. 21A–21C are graphs of the Raman spectrum of artificial and actual aqueous humor samples.
Figure 21B:
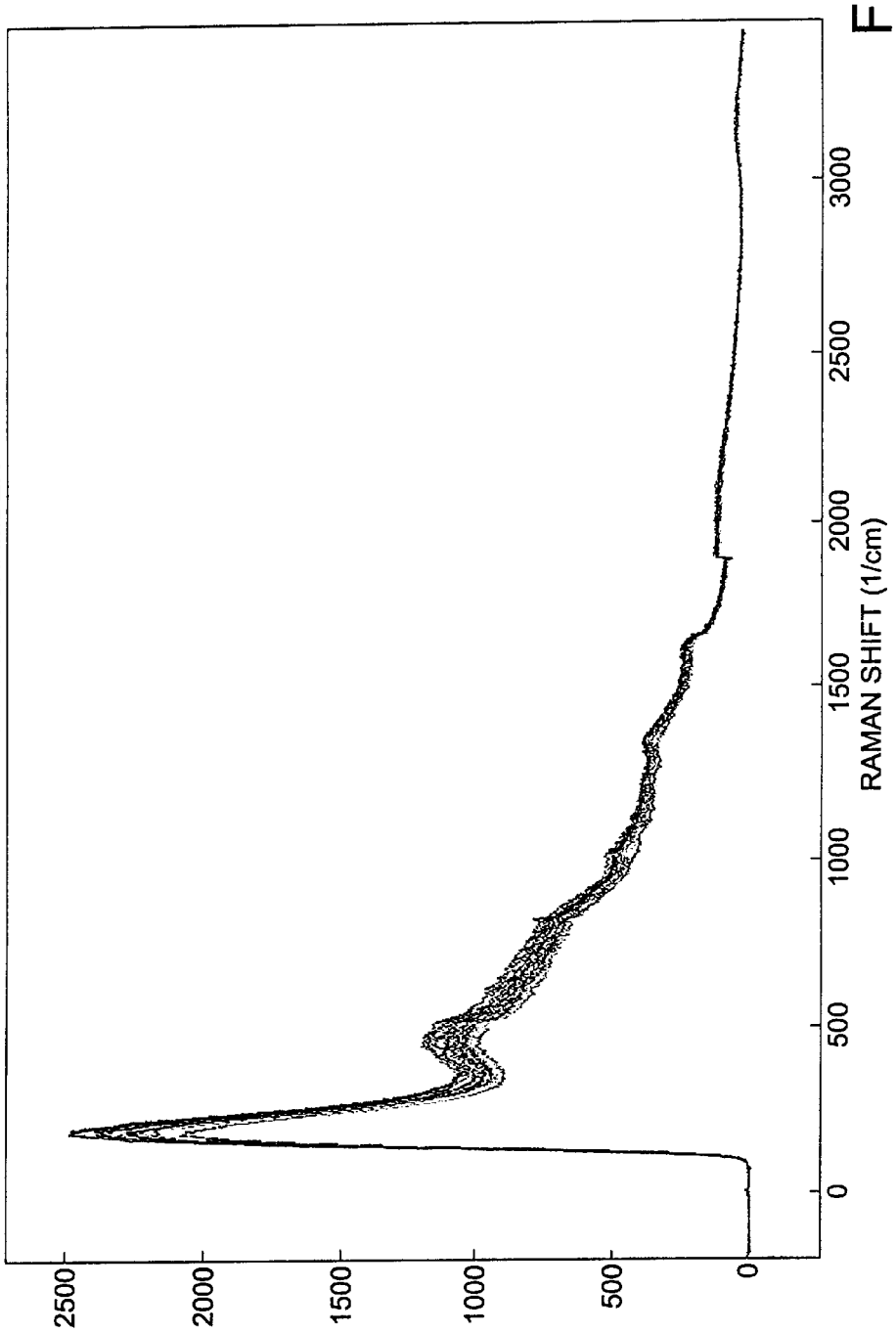
Figure 21C:
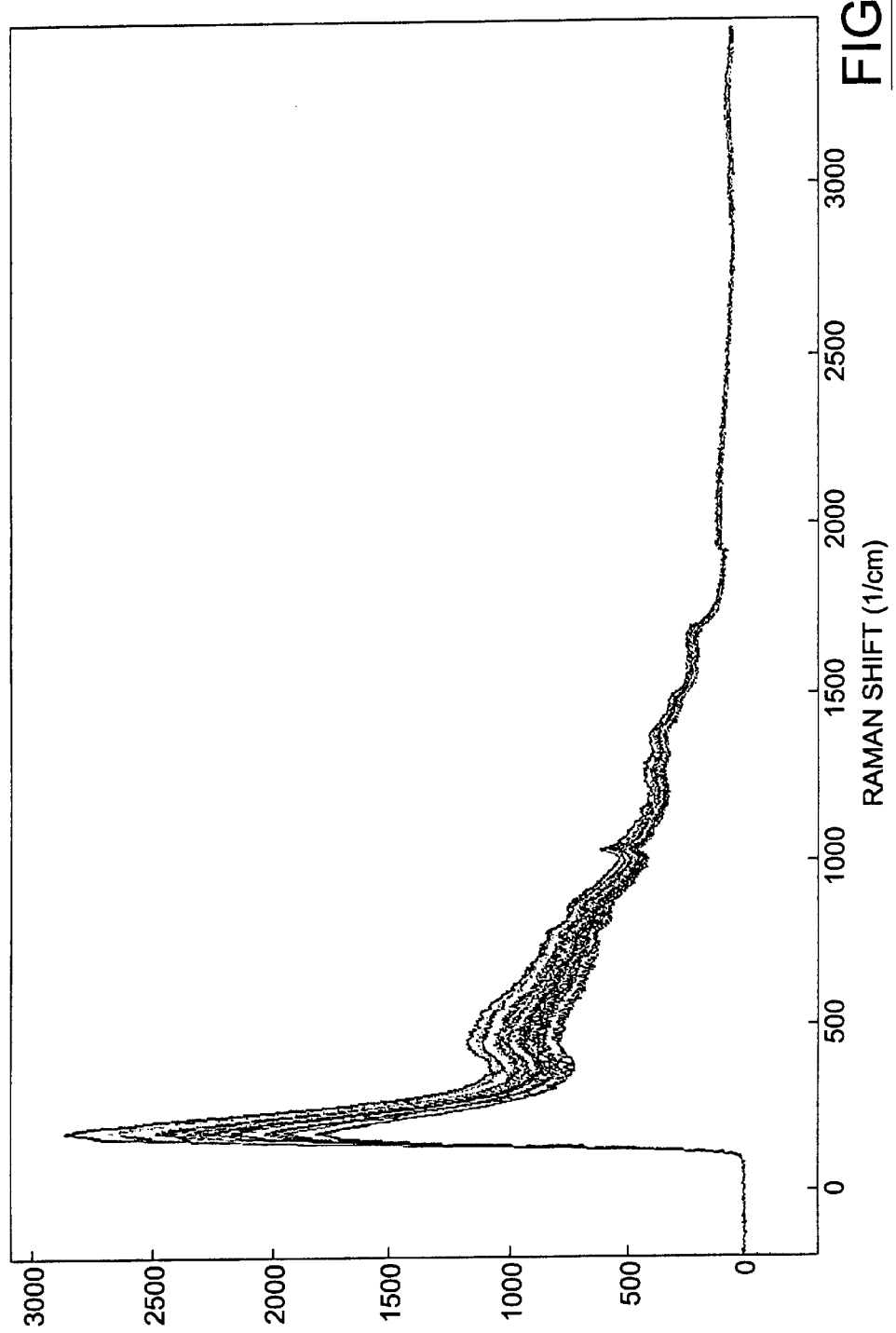

FIGS. 21A–C illustrate experimental results obtained for (a) the spectrum for an artificial in vitro AH in a model anterior chamber (FIG. 21A); (b) the spectrum for an actual in vitro measured (extracted real AH) in a model anterior chamber (FIG. 21B); and (c) the spectrum for an actual in vivo AH measurements (FIG. 21C). A 20× objective with a numerical aperture of about 0.4 was used to obtain the data. The "ensemble" spectra (of the constituents of the AH) correspond well between the three figures. As may be expected, the in vivo and in vitro intensity of the Raman spectra was less than the in vitro artificial sample, but the spectra peaks corresponded well between the measurements (the device able to detect the physiological levels). The in vitro measurements of the AH were obtained using extracted rabbit eyes placed under a contact lens.

EXAMPLE 5

Measurement of Integrity of Blood-Aqueous and Blood-Brain Barriers

The blood-brain and blood-aqueous barriers block passage of large molecules into the cerebrospinal fluid or aqueous humor. Many drugs and disease processes result in disruption of both the blood-aqueous barrier and the blood-brain barrier. In the case of such drugs or disease processes, disruption of the blood-brain barrier can be inferred from breakdown of the blood-aqueous barrier. Breakdown of the blood-aqueous barrier can be measured by measuring the protein content of the aqueous humor or by measuring the concentration of other substances (e.g., drugs) within the aqueous humor. Such substances may be quantifiable by Raman spectroscopy and the protein can be calculated from the fluorescence spectrum since the fluorescence spectrum is largely generated by protein. Consequently, the devices disclosed herein for measuring glucose and other Raman scattering metabolites in the eye can be used for measuring the integrity of the blood-aqueous and blood-brain barriers.

Raman scattering molecules of different sizes that do not normally cross the blood-aqueous or blood-brain barrier could be administered to a patient intravenously. The presence of these molecules is then identified and/or quantified by Raman spectroscopy of the anterior chamber of the eye. This can be used to determine the size of molecules which pass through the blood aqueous barrier. The signature of the Raman spectroscopy signal can then digitally be compared to reference signals (without requiring the use of a difference methodology which would subtract the amount of fluorescence to reveal the Raman spectra of these substances) with the device disclosed herein would reflect the passage of natural proteins through the blood-aqueous and blood brain barriers.

Therapeutic drugs can also be measured to determine their effectiveness in crossing the blood-aqueous or blood-brain barrier.

EXAMPLE 6

Monitoring the Blood Brain Barrier during a Treatment Session

A patient undergoing treatment for a cancer located in the brain or on the other side of the blood brain barrier is administered a non-specific marker which is configured such that it does not normally cross the blood brain barrier (or is reluctant to do so) and which is relatively easily detectable when in the AH by the use of Raman spectroscopic analysis. The blood brain barrier can be altered by administering an osmotic agent such as a chemical substance (such as a drug identified by the trade name "MANATOL" or a similar substance) which acts to physiologically alter the blood brain barrier. In so doing, the blood-aqueous barrier is also altered. In turn, the non-specific marker travels to the AH. An optical measurement can be obtained to confirm that the non-specific marker is indeed in the AH (in a sufficient or elevated quantity to indicate that the blood-aqueous barrier has been altered). The present invention, recognizing that the mechanics of the blood-aqueous barrier and the blood-brain barrier are similar, then presumes that the blood brain barrier has also been altered sufficiently (scale correlation factors may be applied to assure that the blood brain barrier is opened/altered a sufficient amount).

A therapeutic drug (which may be a chemotherapy or cytotoxic drug) can then be administered (injected or otherwise delivered) to the subject. Administering the therapeutic drug after the barrier has been altered can help ensure that the therapeutic drug is not introduced until the blood-brain barrier is altered sufficiently and can allow an elevated amount of the therapeutic drug to pass through the blood-brain barrier over a non-altered state. This can facilitate that more of the drug goes where it is targeted and can reduce the amount in the system of the subject which can often be exposed to undesirable amounts of cytotoxic drugs in conventional treatments in order to ensure that a sufficient amount actually reaches the tumor.

Thus, the present invention now allows one to intentionally break down the barrier and non-invasively confirm the alteration before delivering medicines, which do not normally readily cross the blood brain barrier, to tumors and the like positioned in the blood aqueous or blood brain barrier. Correlations of the amount of the drug administered to the subject, to the amount of the marker administered and detected in the AH, may be established to allow an estimate of the amount of the drug in the spinal fluid or in the blood. Thus, the present invention may also be able to titrate the dose so that the levels in the spinal fluid are sufficiently high but not toxic to the patient in non-targeted regions of the body.

EXAMPLE 7

Measurement of Brain Alcohol Level

A portable device can be used to hold the optical generation and measurement system. The device can be readily carried by police enforcement agencies and conveniently used when a suspect is evaluated for potential DUI infractions. Thus, the device can be positioned over the eye(s) of the subject and the subject can be instructed to read or identify the text or object encoded or displayed as the fixation target in the headset over the eye or eyes. When the subject verbally affirms the proper identification of the fixation target, the device can be operated to obtain a reading. The device may include an auto or manual focus to correct the vision in the device and to allow the subject to focus to the target as needed. Almost instantaneously, the police officer can have quantitative results of the brain alcohol or blood alcohol level of the suspect. The amount or concentration of the alcohol determined to be in the AH (or conjunctiva vessel) can be correlated to either a blood alcohol and/or brain alcohol level. Many states presently regulate blood alcohol levels; however, it is anticipated that an impairment can be assessed also based on either or both blood or brain alcohol levels. As such, the device may generate a plurality of numbers, such as the concentration in the eye, and, the indirectly measured or correlated concentration in the blood and/or brain. If above the legal limit, which can be programmed for each state or locality, a documentary arrest record can be generated with a date and time stamp encoded onto the measurement record which can be automatically generated and electronically stored or printed.

In some embodiments, the Raman spectrum of the subject may include many wavelengths and the determination of the concentration or presence of alcohol may include determining the significant peaks associated with alcohol and subtracting the AH constituents from the signal. It is anticipated that the method and devices will be able to identify blood alcohol and brain alcohol levels between about 0.001–1%, and typically between 0.01–0.8% (noting that concentrations above 1% may be lethal) and that medical assistance may be indicated for certain levels.

EXAMPLE 8

Non-invasive In Vivo Identification of the Presence of Illegal Narcotics

A portable device can be used to hold the optical generation and measurement system. The device can be readily carried by state or federal police enforcement agencies (or hospitals including medical examiners for autopsy) and conveniently used when a suspect is evaluated for potential illegal possession of drugs. In operation, the device can be configured as a headset with the display and light transmission path positioned in front of the eye(s) of the subject. The subject can be instructed to read or identify the text or object encoded or displayed in the device as the fixation target in the headset over the eye or eyes. The device may include an auto or manual focus to correct the vision in the device and to allow the subject to focus to the target as needed. When the subject verbally affirms the proper identification of the fixation target, the device can be operated to obtain a reading. Almost instantaneously, the police officer can have quantitative results of whether the suspect has inhaled, ingested, injected, or otherwise consumed an illegal narcotic. It is anticipated that concentrations in the range of between about 0.001–1% (in the AH) or higher in the conjunctiva vessel (i.e., in the blood volume) may be quantified. Drugs present in small quantities (such as the pico-molar range) may be able to be identified (or the bodies' reaction thereto identified thereby identifying the drug) but may not be able to be reliably quantified.

It is noted that illegal narcotics may vary jurisdiction to jurisdiction and the device can be programmed according to the laws of the jurisdiction of use. Examples of illegal narcotics include opiate-based drugs such as cocaine in several forms such as crack, powder, and the like, and other drugs such as LSD, pcp, angel dust, marijuana, and others. It is anticipated that the most commonly used or street available illegal drugs or abused prescription drugs can be analyzed to predetermine the Raman signature as discussed above and these reference signature standards for these substances stored for reference to the in situ reading obtained on the suspect.

In certain embodiments, the device and method can include assessing both, the brain alcohol (or blood alcohol) level of the suspect, and the presence of an illegal narcotic with one reading. Further, the present invention can be used to develop legal limits for other non-alcohol products so as to ascertain whether an individual is impaired for improved safety on the roadways.

If an illegal narcotic is identified or if the alcohol level is above the legal limit, (the legal limit can be programmed for each state or locality), a documentary arrest record can be generated with a date and time stamp encoded onto the measurement record which can be automatically generated and electronically stored or printed.

EXAMPLE 9

Determination and/or Identification of Drug or Steroid Use

In lieu of conventional urine tests, the present invention can be used to screen potential employees for drug use, or to assure employees are drug or alcohol free prior to allowing them to operate equipment (such as airplanes, trains, buses, subways, or other mass transit systems or heavy equipment and the like). This convenient and non-invasive screening may be a suitable testing system to help assure that the operators entrusted with the lives of others are not operating in an impaired state.

The present invention can also be used to screen athletes for banned substances prior to competitions or at periodic or audit intervals, and/or to screen parolees for violation of parole. Indeed, the readings can be obtained locally and then electronically relayed to a remote monitoring station where the results can be analyzed and proper authorities alerted of a positive test.

EXAMPLE 10

Identification of Ingested Poison(s)

Similar to Example 8, an in situ reading can be taken on an initial evaluation of a poison suspect, either by a paramedic at a home or in route to a hospital, or by a clinician, such as at an Emergency Room, to allow a relatively fast triage assessment of whether one or more poisons are present in the body. One reading may be able to identify one or more of several different signature peaks associated with several different poisons. The poisons may be common household products such as different medications, or a pesticide/herbicide, a cleaning agent, or antifreeze. By pre-evaluating the Raman signature of a plurality of common substances and electronically storing the data associated therewith in an electronic poison control reference library, the methods and devices of the present invention can deconvolute the in situ obtained Raman spectrum signal to build or match a signal pattern with the Raman reference standards. Based upon the substances with signatures, which substantially match the in situ Raman signal, probable or possible substances can be identified (or to exclude other suspect substances). Knowing which of the chemicals or substances have the profile signature closest to the in situ obtained signature, the Raman signal(s) allows for the identification of which poisons may be in the body. The match can be based on a computational comparison of peaks or a graphical comparison. For example, the match can be carried out by matching the peaks or line shape profile across the spectrum of interest via best-fit curves or statistical correlation methods can identify products which align or match that of the data from the subject. A list of substances with associated probability ratings can be provided to the clinician.

In addition, a quantitative determination of the amount of the identified substance or substances in the body may be able to be made depending on the strength of the signal (stronger signals typically indicate higher concentrations).

In one embodiment, the Raman signature of a selected metabolite can be reviewed to see if the level is carcinogenic in the subject. For example, antifreeze (ethylene glycol) can be toxic to the liver. If it is identified that the either ethylene glycol was ingested or that the liver is emitting toxins or products, a treatment such as alcohol can be administered to offset the toxicity of the poison. Similarly, for other embodiments, the substance or drug itself may not be detectable in minute quantities in the body (typically in the pico or micro molar range). However, it may be possible to detect either a constituent of the substance of interest, or a physiologic reaction to the substance, to see if it is in an elevated level in the body (due to the body breaking down or reacting to the substance).

The foregoing is illustrative of the present invention, and is not to be construed as limiting thereof. The invention is defined by the following claims, with equivalents of the claims to be included therein.

We claim:

1. An in vivo method for monitoring the blood brain barrier dynamics of a subject, comprising the step of:

obtaining a Raman spectrum of a selected region in the eye of the subject; and monitoring the dynamics of the blood brain barrier of the subject based on the obtained Raman spectrum.

2. A method according to claim 1, further comprising the step of administering a non-specific marker to the subject selected for its normal reluctance to cross the blood brain barrier under a normal condition, and wherein said monitoring step comprises detecting the presence of the non-specific marker in the selected region of the eye of the subject after the administering step based on the obtained Raman spectrum.

3. A method according to claim 1, further comprising the steps of:
 altering the dynamics of the blood brain barrier of the subject from a normal condition; and
 administering a quantity of a selected therapeutic agent to a subject for treatment of condition in the brain or neurologic system after said altering step.

4. A method according to claim 3, further comprising the step of returning the blood brain barrier to a substantially normal state after a sufficient quantity of the therapeutic agent has been delivered to the brain.

5. A method according to claim 3, wherein said obtaining step is repeated a plurality of times.

6. A method according to claim 3, wherein said obtaining step is performed before said administering step to confirm that the dynamics of the brain have been successfully altered and subsequently to confirm that the blood brain barrier is returned to a substantially normal condition.

7. A method according to claim 3, wherein said method further comprises the step of assessing the dose amount of the therapeutic agent delivered to the brain.

8. A method according to claim 1, wherein the selected region of the eye comprises the aqueous humor.

9. A method according to claim 1, wherein the selected region of the eye comprises the vitreous humor.

10. A method according to claim 1, wherein the selected region of the eye comprises a conjunctive vessel.

11. A method according to claim 1, wherein the therapeutic agent is a cytotoxic agent suitable for treating a cancer in the brain.

12. A method according to claim 3, wherein said altering step is carried out by introducing a chemical to the subject to temporarily open the blood brain barrier which allows larger molecules to pass therethrough.

13. A method according to claim 3, wherein said altering step is carried out by increasing the intracranial pressure of the subject.

14. A method according to claim 3, wherein the therapeutic agent is directed to treating brain cancer.

15. A method of non-invasively monitoring the blood brain barrier of a subject, comprising the steps of:
 generating an excitation beam;
 focusing the excitation beam of said generating step into the eye of the subject so that a selected region is illuminated;
 detecting a Raman spectrum corresponding to the illuminated region; and
 monitoring the blood brain barrier dynamics during exposure to selected conditions based on said detecting step.

16. A method according to claim 15, wherein said monitoring step comprises assessing whether the dynamics of the blood brain barrier are altered sufficiently to allow at least one selected analyte, which would normally be inhibited from traveling through the blood brain barrier, to pass into the intracranial spinal fluid through the blood brain barrier.

17. A method according to claim 16, wherein said method further comprises the steps of:
 administering a non-specific marker to the subject, the non-specific marker being selected for its normal reluctance to pass through the blood brain barrier;
 comparing the Raman spectrum from said detecting step to predetermined reference spectrums corresponding to the non-specific marker; and
 identifying the presence of the non-specific marker in the Raman spectrum of said detecting step to indicate that the dynamics of the blood brain barrier have changed.

18. A method according to claim 17, wherein said detecting step is carried out by illuminating the aqueous humor of the eye.

19. A method according to claim 17, wherein said detecting step is carried out by illuminating the vitreous humor of the eye.

20. A method according to claim 16, wherein said detecting step is carried out when the subject is exposed to elevated ambient pressures.

21. A method according to claim 17, further comprising the step of 30 introducing a cytotoxic agent to the subject after said identifying step.

22. A method according to claim 16, wherein said monitoring step is carried out when the subject is exposed to gravity deficient environments.

23. A method according to claim 16, wherein said method is carried out during drug trials to assess the impact of the drug on the dynamics of the blood brain barrier of the subject.

24. A method according to claim 17, wherein said method is carried out when the brain of the subject has been exposed to a trauma injury to determine whether there is an alteration of the dynamics of the blood brain barrier.

25. A method for identifying an alteration in the blood brain barrier of a biological subject, comprising the steps of:
 non-invasively obtaining a first in vivo Raman spectrum of the aqueous humor of the subject;
 non-invasively obtaining a second in vivo Raman spectrum of the aqueous humor of the subject; and
 comparing the first and second Raman spectrums to detect an alteration in the function of the blood brain barrier.

26. A method for identifying an alteration or abnormality in the blood brain barrier of a biological subject, comprising the steps of:
 non-invasively obtaining a first in vivo Raman spectrum of the aqueous humor of the subject;
 obtaining at least one reference spectrum of an in vitro sample representing the aqueous humor and comprising at least one selected analyte;
 comparing the in vivo Raman spectrum to the reference spectrum; and
 identifying an abnormality in the blood brain barrier based on the detected presence of at least one selected analyte in the aqueous humor based on the comparison of the in vivo and reference Raman spectra.

27. A method according to claim 26, wherein said the least one analyte is a physiological compatible non-specific marker which is selected based on its natural reluctance to pass through the blood brain barrier.

28. A non-invasive method for determining the alcohol level in a subject, comprising the steps of:
 generating an excitation beam;
 focusing the excitation beam of said generating step into the anterior chamber of an eye of the subject so that aqueous humor in the anterior chamber is illuminated;
 detecting a Raman spectrum corresponding to the illuminated aqueous humor;
 comparing the Raman spectrum from said detecting step to reference spectrums corresponding to different concentrations of alcohol; and assessing the brain alcohol level in the subject based on said detecting and comparing steps.

29. A non-invasive method for identifying an unknown poison in a subject, comprising the steps of:
generating an excitation beam;
focusing the excitation beam of said generating step into a selected region in the eye of the subject so that the selected region is illuminated;
detecting a Raman spectrum corresponding to the illuminated selected region;
comparing the Raman spectrum from said detecting step to reference spectra corresponding to different concentrations of a plurality of different substances; and
identifying the unknown substance in the subject based on said detecting and comparing steps, wherein the selected region of the eye is one of the aqueous humor and a conjunctiva vessel, said method further comprising the step of estimating the amount of the at least one analyte of interest in the cerebral spinal fluid of the subject based on said detecting, comparing, and identifying steps.

30. A method for non-invasively directly measuring the blood level of a substance of interest in a subject, comprising the steps of:
obtaining a plurality of reference Raman spectrums of varying concentrations of at least one analyte of interest;
generating an excitation beam;
focusing the excitation beam of said generating step into at least one conjunctiva vessel in the eye of the subject so that the vessel is illuminated;
detecting a Raman spectrum corresponding to the illuminated vessel;
comparing the Raman spectrum from said detecting step to the reference spectrums; and
determining the blood level of the at least one analyte based on said detecting and comparing steps.

31. A method according to claim 30, wherein the reference spectrums comprise a plurality of different Raman spectrums generated for each of the at least one analyte at different concentrations based on in vitro samples thereof.

32. A method according to claim 30, wherein said excitation beam pulse is low energy.

33. A method according to claim 30, wherein said at least one analyte is glucose.

34. A method according to claim 30, wherein said at least one analyte is a plurality of different selected analytes, and wherein said method further comprises, for a single detecting step, identifying the presence of at least one of the different plurality of substances in the subject.

35. A method according to claim 30, wherein said at least one analyte is alcohol.

36. A method according to claim 30, further comprising the step of subtracting a fluorescence spectrum from said vessel Raman spectrum to produce a difference spectrum.

37. A method according to claim 28, wherein said identifying step identifies an elevated antibody level in the subject.

38. A method according to claim 28, wherein said identifying step detects the presence of a poison in the subject.

39. A method according to claim 28, wherein the reference spectra of selected analytes of interest are based on selected household chemicals.

40. A method according to claim 28, wherein the reference spectra of selected analytes of interest are of illegal narcotics.

41. A method according to claim 28, wherein said reference spectra for each analyte of interest comprises spectra generated from a Raman spectra training set comprising at least 10 in vitro aqueous humor samples for each analyte of interest with each of the at least 10 samples including different amounts of the analyte therein, and an analyte level corresponding to each of the samples.

42. An apparatus for the non-invasive determination of a level of an analyte of interest in a subject, comprising:
a light source for generating an excitation beam;
an optical system operatively associated with said laser for directing said excitation beam into the eye of said subject so that a selected region in the eye is sufficiently illuminated to generate a detectable Raman spectrum thereof;
a detector operatively associated with said optical system and configured to detect a Raman spectrum from the selected region in the eye;
a system processor operably associated with said detector and including computer programs with computer program code for comparing the detected Raman spectrum signal to reference spectrums associated with at least one analyte of interest to identify the presence or absence of at least one analyte of interest in the subject, wherein said system processor comprises computer program code for determining the in vivo brain level of at least one analyte of interest for the subject based on the detected Raman spectrum;
a housing configured to overlie at least one eye of a subject during use and to house said optical system and said detector therein, so that, in position, the optical system is spaced apart from the eye of the subject; and
a focus adjustment unit including a visual display adapted to display visual indicia thereon, mounted in said housing so that, in operation, the visual indicia on said display is visible to a user to allow a user to look at a visual reference presented thereon to allow the visual indicia to be focused so that the excitation beam can be directed to the appropriate location in the eye of the subject and so that said detector can detect the generated Raman spectrum.

43. An apparatus according to claim 35, wherein said system processor comprises means for subtracting a fluorescence spectrum for said Raman spectrum to produce a difference spectrum.

44. An apparatus according to claim 35, wherein said optical system is configured to illuminate the aqueous humor of the eye.

45. An apparatus according to claim 35, wherein said optical system is configured to illuminate the vitreous humor of the eye.

46. An apparatus for the non-invasive determination of a blood level of an analyte of interest in a subject, comprising:
a light source for generating an excitation beam;
an optical system operatively associated with said laser for directing said excitation beam into the eye of said subject so that a selected region in the eye is sufficiently illuminated to generate a detectable Raman spectrum thereof, wherein said optical system is configured to illuminate at least one blood vessel in the conjunctiva of the eye;
a detector operatively associated with said optical system and configured to detect a Raman spectrum from the at least one blood vessel in the conjunctiva of the eye;
a system processor operably associated with said detector and including computer programs with computer program code for comparing the detected Raman spectrum signal to reference spectrums associated with at least one analyte of interest to identify the presence or absence of at least one analyte of interest in the subject;

a housing configured to overlie at least one eye of a subject during use and to house said optical system and said detector therein, so that, in position, the optical system is spaced apart from the eye of the subject; and a focus adjustment unit including a visual display adapted to display visual indicia thereon, mounted in said housing so that, in operation, the visual indicia on said display is visible to a user to allow a user to look at a visual reference presented thereon to allow the visual indicia to be focused so that the excitation beam can be directed to the appropriate location in the eye of the subject and so that said detector can detect the generated Raman spectrum.

47. An apparatus according to claim 39, wherein said excitation beam has a wavelength of from about 600 to 900 nanometers.

48. An apparatus according to claim 39, wherein said excitation beam is low energy.

49. An apparatus according to claim 39, wherein said excitation beam has a wavelength of about 633 nm.

50. An apparatus according to claim 39, wherein the computer program reference spectrums are produced with a training set of Raman spectra corresponding to at least 20 aqueous humor samples of varying concentrations of analytes therein for each of a plurality of different selected analytes and an identified blood level of said analyte of interest for each of said samples.

51. An apparatus according to claim 50, wherein said analyte of interest is alcohol.

52. An apparatus according to claim 35, wherein said at least one analyte is cytotoxic and/or a poison.

53. An apparatus according to claim 42, wherein said the poison comprises at least one of a household chemical, pesticide, herbicide, or petroleum product.

54. An apparatus according to claim 35, wherein said at least one analyte is from a poisonous plant.

55. An apparatus according to claim 35, wherein said at least one analyte is a drug.

56. An apparatus according to claim 35, wherein said housing is configured and sized to fit onto and rest against the head of the subject during operation.

57. An apparatus according to claim 40, wherein said housing is configured and sized to be a hand held device.

* * * * *